US010385324B2

(12) United States Patent
Díez García et al.

(10) Patent No.: US 10,385,324 B2
(45) Date of Patent: Aug. 20, 2019

(54) VARIANTS OF CELLOBIOHYDROLASE 1

(71) Applicant: ABENGOA BIOENERGÍA NUEVAS TECNOLOGÍAS, S.A., Seville (ES)

(72) Inventors: Bruno Díez García, Seville (ES); Noelia Valbuena Crespo, Seville (ES); Francisco Manuel Reyes Sosa, Seville (ES); Antonio Javier Moreno Pérez, Seville (ES); Dolores Pérez Gómez, Seville (ES); Ana Isabel Platero Gómez, Seville (ES); Lucia Martín Pérez, Seville (ES); Sandra Gavaldá Martín, Seville (ES); Laura Viñas De La Cruz, Seville (ES); Laura Sánchez Zamorano, Seville (ES); Consolación Álvarez Núñez, Seville (ES); María de los Ángeles Bermúdez Alcántara, Seville (ES); Javier Rocha Martín, Seville (ES); Laura Ledesma García, Seville (ES); Juan Luis Ramos Martín, Seville (ES); Laura Benítez Casanova, Seville (ES); Macarena López Morales, Seville (ES)

(73) Assignee: ABENGOA BIOENERGÍA NUEVAS TECNOLOGÍAS, S.A., Seville (ES)

( * ) Notice: Subject to any disclaimer, the term of this patent is extended or adjusted under 35 U.S.C. 154(b) by 0 days.

(21) Appl. No.: 15/564,486

(22) PCT Filed: Apr. 8, 2016

(86) PCT No.: PCT/ES2016/070243
§ 371 (c)(1),
(2) Date: Jan. 23, 2018

(87) PCT Pub. No.: WO2016/162587
PCT Pub. Date: Oct. 13, 2016

(65) Prior Publication Data
US 2018/0142225 A1    May 24, 2018

(30) Foreign Application Priority Data
Apr. 8, 2015  (ES) .................................. 201530467

(51) Int. Cl.
*C12N 9/42*     (2006.01)
*C12P 19/02*    (2006.01)
*C12P 7/10*     (2006.01)
*C12P 19/14*    (2006.01)
*C12N 9/24*     (2006.01)

(52) U.S. Cl.
CPC ............. *C12N 9/2437* (2013.01); *C12N 9/24* (2013.01); *C12P 7/10* (2013.01); *C12P 19/02* (2013.01); *C12P 19/14* (2013.01); *C12Y 302/01091* (2013.01); *Y02E 50/16* (2013.01)

(58) Field of Classification Search
None
See application file for complete search history.

(56) References Cited

U.S. PATENT DOCUMENTS

| 2009/0162916 A1* | 6/2009 | Adney | C12Y 302/01091 435/209 |
| 2012/0003703 A1* | 1/2012 | Mitchell | C12N 9/2437 435/99 |

FOREIGN PATENT DOCUMENTS

| WO | WO 2011143632 A2 | 11/2011 |
| WO | WO 2012/048171 A2 | 4/2012 |
| WO | WO 2012/051055 A2 | 4/2012 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Alignment SEQ ID No. 2 to US20090280105 SEQ ID No. 4. (Year: 2012).*
Alignment SEQ ID No. 6 to US20090280105 SEQ ID No. 2. (Year: 2012).*
Alignment SEQ ID No. 9 to US20090280105 SEQ ID No. 2. (Year: 2012).*
J. Devereux, et al., A comprehensive set of sequence analysis programs for the VAX, Nucleic Acids Research, vol. 12, No. 1, 1984, pp. 387, 395.
J. Verdoes, et al., A dedicated vector for efficient library construction and high throughput screening in the hyphal fungus *Chrysosporium lucknowense*, Industrial Biotechnology, Mar. 2007, 2 pages.
S. Altschul, et al., Basic Local Alignment Search Tool, J. Mol. Biol. (1990), 215, pp. 403-410.
D. G. Higgins and P. M. Sharp, Fast and sensitive multiple sequence alignments on a microcomputer, Bioinformatics, vol. 5, No. 2, pp. 151-153, Apr. 1989.
N. Mosier, et al., Features of promising technologies for pretreatment of lignocellulosic biomass, Bioresource Technology, 96 (2005), 673-686.

(Continued)

*Primary Examiner* — Christian L Fronda
(74) *Attorney, Agent, or Firm* — Leason Ellis LLP

(57) ABSTRACT

The present invention relates to variants of cellobiohydrolase, preferably Cbh1, which have greater cellobiohydrolase activity. The invention also relates to a genetic construct, a host cell and to an enzyme composition comprising said variants. The invention further relates to a procedure for producing fermentable sugar and a procedure for producing a bioproduct, such as bioethanol, from cellulose material with the cellobiohydrolase variants, the host cell or the enzyme composition comprising said variants.

18 Claims, 12 Drawing Sheets

Specification includes a Sequence Listing.

(56) References Cited

OTHER PUBLICATIONS

S. F. Altschul, et al., Gapped BLAST and PSI-BLAST: a new generation of protein database search programs, Nucleic Acids Research, 1997, vol. 25, No. 17, 3389-3402.
R. Kittl, et al., Production of four Neurospora crassa lytic polysaccharide monooxygenases in Pichia pastoris monitored by a fluorimetric assay, Biotechnology for Biofuels, 2012, 5:79.
W. J. Wilbur, et al., Rapid similarity searches of nucleic acid and protein data banks, Proc. Natl. Acad. Sci. USA, vol. 80, pp. 726-730, Feb. 1983.
J. Woodward, Synergism in Cellulase Systems, Bioresource Technology, 36 (1991), 67-75.
International Preliminary Report on Patentability in corresponding PCT Application No. PCT/ES2016/070243, dated Oct. 10, 2017.
International Search Report and Written Opinion in corresponding PCT Application No. PCT/ES2016/070243, dated May 27, 2016.
Adney, W.S. et al., "Probing the role of N-linked glycans in the stability and activity of fungal cellobiohydrolases by mutational analysis" Cellulose, Aug. 2009, vol. 16, No. 4, pp. 699-709.
Gusakov, A.V. et al, "N-Glycosylation in Chrysosporium lucknowense enzymes" Carbohydrate Research, Jan. 14, 2008, vol. 343, No. 1, pp. 48-55.
Karnaouri, A. et al. "Genomic insights into the fungal lignocellulolytic system of Myceliophthora thermophila". Frontiers in Microbiology, Jun. 18, 2014. vol. 5, articulo 281, pp. 1-22.
Visser, H. et al. "Development of a mature fungal technology and production platform for industrial enzymes based on a Myceliophthora thermophila isolate, previously known as Chrysosporium lucknowense C1". Industrial Biotechnology, Jun. 2011, vol. 7, N° 3, pp. 214-223.

\* cited by examiner

SEQUENCE LISTING

```
<160> NUMBER OF SEQ ID NOS: 19

<210> SEQ ID NO 1
<211> LENGTH: 1648
<212> TYPE: DNA
<213> ORGANISM: Myceliophthora thermophila

<400> SEQUENCE: 1
atgtacgcca agttcgcgac cctcgccgcc cttgtggctg gcgccgctgc tcagaacgcc      60
tgcactctga ccgctgagaa ccaccoctcg ctgacgtggt ccaagtgcac gtctggcggc     120
agctgcacca gcgtccaggg ttccatcacc atcgacgcca actggcggtg gactcaccgg     180
accgatagcg ccaccaactg ctacgagggc aacaagtggg atacttcgta ctgcagcgat     240
ggtccttctt gcgcctccaa gtgctgcatc gacgcgctg actactcgag cacctatggc     300
atcaccacga gcggtaactc cctgaacctc aagttcgtca ccaagggcca gtactcgacc     360
aacatcggct cgcgtaccta cctgatggag agcgacacca agtaccagag taagttcctc     420
tcgcacccgg ccgccgggag atgatggcgc ccagcccgct gacgcgaatg acacagtgtt     480
ccagctcctc ggcaacgagt tcaccttcga tgtcgacgtc tccaacctcg gctgcggcct     540
caatggcgcc ctctacttcg tgtccatgga tgccgatggt ggcatgtcca agtactcggg     600
caacaaggca ggtgccaagt acggtaccgg ctactgtgat tctcagtgcc cccgcgacct     660
caagttcatc aacggcgagg ccaacgtaga gaactggcag agctcgacca acgatgccaa     720
cgccggcacg ggcaagtacg gcagctgctg ctccgagatg gacgtctggg aggccaacaa     780
catggccgcc gccttcactc cccacccttg caccgtgatc ggccagtcgc gctgcgaggg     840
cgactcgtgc ggcggtacct acagcaccga ccgctatgcc ggcatctgcg accccgacgg     900
atgcgacttc aactcgtacc gccagggcaa caagaccttc tacggcaagg gcatgacggt     960
cgacacgacc aagaagatca cggtcgtcac ccagttcctc aagaactcgg ccggcgagct    1020
ctccgagatc aagcggttct acgtccagaa cggcaaggtc atccccaact ccgagtccac    1080
```

```
catcccgggc gtcgagggca actccatcac ccaggactgg tgcgaccgcc agaaggccgc    1140
cttcggcgac gtgaccgact tccaggacaa gggcggcatg gtccagatgg caaggcccct    1200
cgcggggccc atggtcctcg tcatgtccat ctgggacgac cacgccgtca acatgctctg    1260
gctcgactcc acctggccca tcgacggcgc cggcaagccg ggcgccgagc gcggtgcctg    1320
ccccaccacc tcgggcgtcc ccgctgaggt cgaggccgag gccccaact ccaacgtcat    1380 cttctccaac atccgcttcg gccccatcgg ctccaccgtc tccggcctgc ccgacggcgg    1440
cagcggcaac cccaacccgc ccgtcagctc gtccaccccg gtccctcct cgtccaccac    1500 atcctccggt tcctccggcc cgactggcgg cacgggtgtc gctaagcact atgagcaatg    1560
cggaggaatc gggttcactg gccctaccca gtgcgagagc ccctacactt gcaccaagct    1620
gaatgactgg tactcgcagt gcctgtaa                                       1648

<210> SEQ ID NO 2
<211> LENGTH: 526
<212> TYPE: PRT
<213> ORGANISM: Myceliophthora thermophila
<220> FEATURE:
<221> NAME/KEY: SIGNAL
<222> LOCATION: (1)..(17)

<400> SEQUENCE: 2

Met Tyr Ala Lys Phe Ala Thr Leu Ala Ala Leu Val Ala Gly Ala Ala
1               5                   10                  15

Ala Gln Asn Ala Cys Thr Leu Thr Ala Glu Asn His Pro Ser Leu Thr
                20                  25                  30

Trp Ser Lys Cys Thr Ser Gly Gly Ser Cys Thr Ser Val Gln Gly Ser
            35                  40                  45

Ile Thr Ile Asp Ala Asn Trp Arg Trp Thr His Arg Thr Asp Ser Ala
        50                  55                  60

Thr Asn Cys Tyr Glu Gly Asn Lys Trp Asp Thr Ser Tyr Cys Ser Asp
65                  70                  75                  80

Gly Pro Ser Cys Ala Ser Lys Cys Cys Ile Asp Gly Ala Asp Tyr Ser
                85                  90                  95

Ser Thr Tyr Gly Ile Thr Thr Ser Gly Asn Ser Leu Asn Leu Lys Phe
                100                 105                 110

Val Thr Lys Gly Gln Tyr Ser Thr Asn Ile Gly Ser Arg Thr Tyr Leu
            115                 120                 125

Met Glu Ser Asp Thr Lys Tyr Gln Met Phe Gln Leu Leu Gly Asn Glu
        130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Ala Asp Gly Gly Met Ser Lys Tyr
                165                 170                 175

Ser Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Val Glu
        195                 200                 205

Asn Trp Gln Ser Ser Thr Asn Asp Ala Asn Ala Gly Thr Gly Lys Tyr
    210                 215                 220

Gly Ser Cys Cys Ser Glu Met Asp Val Trp Glu Ala Asn Asn Met Ala
225                 230                 235                 240

Ala Ala Phe Thr Pro His Pro Cys Thr Val Ile Gly Gln Ser Arg Cys
                245                 250                 255
```

```
Glu Gly Asp Ser Cys Gly Gly Thr Tyr Ser Thr Asp Arg Tyr Ala Gly
            260                 265                 270

Ile Cys Asp Pro Asp Gly Cys Asp Phe Asn Ser Tyr Arg Gln Gly Asn
        275                 280                 285

Lys Thr Phe Tyr Gly Lys Gly Met Thr Val Asp Thr Thr Lys Lys Ile
    290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Glu Gly Asn Ser Ile Thr Gln Asp Trp Cys
            340                 345                 350

Asp Arg Gln Lys Ala Ala Phe Gly Asp Val Thr Asp Phe Gln Asp Lys
        355                 360                 365

Gly Gly Met Val Gln Met Gly Lys Ala Leu Ala Gly Pro Met Val Leu
    370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                405                 410                 415

Ala Cys Pro Thr Thr Ser Gly Val Pro Ala Glu Val Glu Ala Glu Ala
            420                 425                 430

Pro Asn Ser Asn Val Ile Phe Ser Asn Ile Arg Phe Gly Pro Ile Gly
        435                 440                 445

Ser Thr Val Ser Gly Leu Pro Asp Gly Ser Gly Asn Pro Asn
    450                 455                 460

Pro Val Ser Ser Thr Pro Val Pro Ser Ser Thr Thr Ser Ser
465                 470                 475                 480

Gly Ser Ser Gly Pro Thr Gly Thr Gly Val Ala Lys His Tyr Glu
                485                 490                 495

Gln Cys Gly Gly Ile Gly Phe Thr Gly Pro Thr Gln Cys Glu Ser Pro
            500                 505                 510

Tyr Thr Cys Thr Lys Leu Asn Asp Trp Tyr Ser Gln Cys Leu
        515                 520                 525

<210> SEQ ID NO 3
<211> LENGTH: 509
<212> TYPE: PRT
<213> ORGANISM: Myceliophthora thermophila

<400> SEQUENCE: 3

Gln Asn Ala Cys Thr Leu Thr Ala Glu Asn His Pro Ser Leu Thr Trp
1               5                   10                  15

Ser Lys Cys Thr Ser Gly Gly Ser Cys Thr Ser Val Gln Gly Ser Ile
                20                  25                  30

Thr Ile Asp Ala Asn Trp Arg Trp Thr His Arg Thr Asp Ser Ala Thr
            35                  40                  45

Asn Cys Tyr Glu Gly Asn Lys Trp Asp Thr Ser Tyr Cys Ser Asp Gly
        50                  55                  60

Pro Ser Cys Ala Ser Lys Cys Cys Ile Asp Gly Ala Asp Tyr Ser Ser
65                  70                  75                  80

Thr Tyr Gly Ile Thr Thr Ser Gly Asn Ser Leu Asn Leu Lys Phe Val
                85                  90                  95

Thr Lys Gly Gln Tyr Ser Thr Asn Ile Gly Ser Arg Thr Tyr Leu Met
```

```
                100             105             110
Glu Ser Asp Thr Lys Tyr Gln Met Phe Gln Leu Leu Gly Asn Glu Phe
        115                 120                 125

Thr Phe Asp Val Asp Val Ser Asn Leu Gly Cys Gly Leu Asn Gly Ala
        130                 135                 140

Leu Tyr Phe Val Ser Met Asp Ala Asp Gly Gly Met Ser Lys Tyr Ser
145                 150                 155                 160

Gly Asn Lys Ala Gly Ala Lys Tyr Gly Thr Gly Tyr Cys Asp Ser Gln
                165                 170                 175

Cys Pro Arg Asp Leu Lys Phe Ile Asn Gly Glu Ala Asn Val Glu Asn
                180                 185                 190

Trp Gln Ser Ser Thr Asn Asp Ala Asn Ala Gly Thr Gly Lys Tyr Gly
                195                 200                 205

Ser Cys Cys Ser Glu Met Asp Val Trp Glu Ala Asn Asn Met Ala Ala
        210                 215                 220

Ala Phe Thr Pro His Pro Cys Thr Val Ile Gly Gln Ser Arg Cys Glu
225                 230                 235                 240

Gly Asp Ser Cys Gly Gly Thr Tyr Ser Thr Asp Arg Tyr Ala Gly Ile
                245                 250                 255

Cys Asp Pro Asp Gly Cys Asp Phe Asn Ser Tyr Arg Gln Gly Asn Lys
                260                 265                 270

Thr Phe Tyr Gly Lys Gly Met Thr Val Asp Thr Thr Lys Lys Ile Thr
        275                 280                 285

Val Val Thr Gln Phe Leu Lys Asn Ser Ala Gly Glu Leu Ser Glu Ile
290                 295                 300

Lys Arg Phe Tyr Val Gln Asn Gly Lys Val Ile Pro Asn Ser Glu Ser
305                 310                 315                 320

Thr Ile Pro Gly Val Glu Gly Asn Ser Ile Thr Gln Asp Trp Cys Asp
                325                 330                 335

Arg Gln Lys Ala Ala Phe Gly Asp Val Thr Asp Phe Gln Asp Lys Gly
                340                 345                 350

Gly Met Val Gln Met Gly Lys Ala Leu Ala Gly Pro Met Val Leu Val
        355                 360                 365

Met Ser Ile Trp Asp Asp His Ala Val Asn Met Leu Trp Leu Asp Ser
        370                 375                 380

Thr Trp Pro Ile Asp Gly Ala Gly Lys Pro Gly Ala Glu Arg Gly Ala
385                 390                 395                 400

Cys Pro Thr Thr Ser Gly Val Pro Ala Glu Val Glu Ala Glu Ala Pro
                405                 410                 415

Asn Ser Asn Val Ile Phe Ser Asn Ile Arg Phe Gly Pro Ile Gly Ser
                420                 425                 430

Thr Val Ser Gly Leu Pro Asp Gly Gly Ser Gly Asn Pro Asn Pro Pro
        435                 440                 445

Val Ser Ser Ser Thr Pro Val Pro Ser Ser Thr Thr Ser Ser Gly
450                 455                 460

Ser Ser Gly Pro Thr Gly Gly Thr Gly Val Ala Lys His Tyr Glu Gln
465                 470                 475                 480

Cys Gly Gly Ile Gly Phe Thr Gly Pro Thr Gln Cys Glu Ser Pro Tyr
                485                 490                 495

Thr Cys Thr Lys Leu Asn Asp Trp Tyr Ser Gln Cys Leu
                500                 505

<210> SEQ ID NO 4
```

<211> LENGTH: 1648
<212> TYPE: DNA
<213> ORGANISM: Artificial Sequence
<220> FEATURE:
<223> OTHER INFORMATION: Polynucleotide that encodes for the mutant
      Cbh1N209D preprotein of SEQ ID NO: 5

<400> SEQUENCE: 4

```
atgtacgcca agttcgcgac cctcgccgcc cttgtggctg gcgccgctgc tcagaacgcc      60
tgcactctga ccgctgagaa ccaccccteg ctgacgtggt ccaagtgcac gtctggcggc     120
agctgcacca gcgtccaggg ttccatcacc atcgacgcca actggcggtg gactcaccgg     180
accgatagcg ccaccaactg ctacgagggc aacaagtggg atacttcgta ctgcagcgat     240
ggtccttctt gcgcctccaa gtgctgcatc gacggcgctg actactcgag cacctatggc     300
atcaccacga gcggtaactc cctgaacctc aagttcgtca ccaagggcca gtactcgacc     360
aacatcggct cgcgtaccta cctgatggag agcgacacca gtaccagag taagttcctc      420
tcgcacccgg ccgccgggag tgatggcgc cagcccgct gacgcgaatg acacagtgtt       480
ccagctcctc ggcaacgagt tcaccttcga tgtcgacgtc tccaacctcg gctgcggcct     540
caatggcgcc ctctacttcg tgtccatgga tgccgatggt ggcatgtcca agtactcggg     600
caacaaggca ggtgccaagt acggtaccgg ctactgtgat tctcagtgcc ccgcgacct      660
caagttcatc aacggcgagg ccaacgtaga ggactggcag agctcgacca acgatgccaa     720
cgccggcacg ggcaagtacg gcagctgctg ctccgagatg gacgtctggg aggccaacaa     780
catggccgcc gccttcactc cccacccttg caccgtgatc ggccagtcgc gctgcgaggg     840
cgactcgtgc ggcggtacct acagcaccga ccgctatgcc ggcatctgcg accccgacgg     900
atgcgacttc aactcgtacc gccagggcaa caagaccttc tacggcaagg catgacggt      960
cgacacgacc aagaagatca cggtcgtcac ccagttcctc aagaactcgg ccggcgagct    1020
ctccgagatc aagcggttct acgtccagaa cggcaaggtc atcccaact ccgagtccac     1080
catcccgggc gtcgagggca actccatcac ccaggactgg tgcgaccgcc agaaggccgc    1140
cttcggcgac gtgaccgact ccaggacaa gggcggcatg gtccgatgg caaggccct      1200
cgcgggcccc atggtcctcg tcatgtccat ctggacgac cacgccgtca acatgctctg     1260
gctcgactcc acctggccca tcgacggcgc cggcaagccg ggcgccgagc gcggtgcctg    1320
ccccaccacc tcgggcgtcc ccgctgaggt cgaggccgag gccccaact ccaacgtcat     1380
cttctccaac atccgcttcg gcccatcgg ctccaccgtc tccggcctgc cgacggcgg     1440
cagcggcaac cccaacccgc ccgtcagctc gtccaccccg gtccctcct cgtccaccac    1500
atcctccggt tcctccggcc cgactggcgg cacgggtgtc gctaagcact atgagcaatg    1560
cggaggaatc gggttcactg gccctaccca gtgcgagagc ccctacactt gcaccaagct    1620
gaatgactgg tactcgcagt gcctgtaa                                       1648
```

<210> SEQ ID NO 5
<211> LENGTH: 526
<212> TYPE: PRT
<213> ORGANISM: Artificial Sequence
<220> FEATURE:
<223> OTHER INFORMATION: Preprotein of the Cbh1 mutant Cbh1N209D
<220> FEATURE:
<221> NAME/KEY: SIGNAL
<222> LOCATION: (1)..(17)

<400> SEQUENCE: 5

Met Tyr Ala Lys Phe Ala Thr Leu Ala Ala Leu Val Ala Gly Ala Ala

-continued

```
1               5                   10                  15
Ala Gln Asn Ala Cys Thr Leu Thr Ala Glu Asn His Pro Ser Leu Thr
                20                  25                  30

Trp Ser Lys Cys Thr Ser Gly Gly Ser Cys Thr Ser Val Gln Gly Ser
            35                  40                  45

Ile Thr Ile Asp Ala Asn Trp Arg Trp Thr His Arg Thr Asp Ser Ala
        50                  55                  60

Thr Asn Cys Tyr Glu Gly Asn Lys Trp Asp Thr Ser Tyr Cys Ser Asp
65                  70                  75                  80

Gly Pro Ser Cys Ala Ser Lys Cys Cys Ile Asp Gly Ala Asp Tyr Ser
                85                  90                  95

Ser Thr Tyr Gly Ile Thr Thr Ser Gly Asn Ser Leu Asn Leu Lys Phe
                100                 105                 110

Val Thr Lys Gly Gln Tyr Ser Thr Asn Ile Gly Ser Arg Thr Tyr Leu
            115                 120                 125

Met Glu Ser Asp Thr Lys Tyr Gln Met Phe Gln Leu Leu Gly Asn Glu
        130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Ala Asp Gly Gly Met Ser Lys Tyr
                165                 170                 175

Ser Gly Asn Lys Ala Gly Ala Lys Tyr Gly Thr Gly Tyr Cys Asp Ser
                180                 185                 190

Gln Cys Pro Arg Asp Leu Lys Phe Ile Asn Gly Glu Ala Asn Val Glu
            195                 200                 205

Asp Trp Gln Ser Ser Thr Asn Asp Ala Asn Ala Gly Thr Gly Lys Tyr
        210                 215                 220

Gly Ser Cys Cys Ser Glu Met Asp Val Trp Glu Ala Asn Asn Met Ala
225                 230                 235                 240

Ala Ala Phe Thr Pro His Pro Cys Thr Val Ile Gly Gln Ser Arg Cys
                245                 250                 255

Glu Gly Asp Ser Cys Gly Gly Thr Tyr Ser Thr Asp Arg Tyr Ala Gly
                260                 265                 270

Ile Cys Asp Pro Asp Gly Cys Asp Phe Asn Ser Tyr Arg Gln Gly Asn
            275                 280                 285

Lys Thr Phe Tyr Gly Lys Gly Met Thr Val Asp Thr Thr Lys Lys Ile
        290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Glu Gly Asn Ser Ile Thr Gln Asp Trp Cys
                340                 345                 350

Asp Arg Gln Lys Ala Ala Phe Gly Asp Val Thr Asp Phe Gln Asp Lys
            355                 360                 365

Gly Gly Met Val Gln Met Gly Lys Ala Leu Ala Gly Pro Met Val Leu
        370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                405                 410                 415

Ala Cys Pro Thr Thr Ser Gly Val Pro Ala Glu Val Glu Ala Glu Ala
                420                 425                 430
```

```
Pro Asn Ser Asn Val Ile Phe Ser Asn Ile Arg Phe Gly Pro Ile Gly
        435                 440                 445

Ser Thr Val Ser Gly Leu Pro Asp Gly Gly Ser Gly Asn Pro Asn Pro
    450                 455                 460

Pro Val Ser Ser Ser Thr Pro Val Pro Ser Ser Thr Thr Ser Ser
465                 470                 475                 480

Gly Ser Ser Gly Pro Thr Gly Gly Thr Gly Val Ala Lys His Tyr Glu
                485                 490                 495

Gln Cys Gly Gly Ile Gly Phe Thr Gly Pro Thr Gln Cys Glu Ser Pro
                500                 505                 510

Tyr Thr Cys Thr Lys Leu Asn Asp Trp Tyr Ser Gln Cys Leu
        515                 520                 525

<210> SEQ ID NO 6
<211> LENGTH: 509
<212> TYPE: PRT
<213> ORGANISM: Artificial Sequence
<220> FEATURE:
<223> OTHER INFORMATION: Mature protein Cbh1N209D

<400> SEQUENCE: 6

Gln Asn Ala Cys Thr Leu Thr Ala Glu Asn His Pro Ser Leu Thr Trp
1               5                   10                  15

Ser Lys Cys Thr Ser Gly Gly Ser Cys Thr Ser Val Gln Gly Ser Ile
            20                  25                  30

Thr Ile Asp Ala Asn Trp Arg Trp Thr His Arg Thr Asp Ser Ala Thr
        35                  40                  45

Asn Cys Tyr Glu Gly Asn Lys Trp Asp Thr Ser Tyr Cys Ser Asp Gly
50                  55                  60

Pro Ser Cys Ala Ser Lys Cys Cys Ile Asp Gly Ala Asp Tyr Ser Ser
65                  70                  75                  80

Thr Tyr Gly Ile Thr Thr Ser Gly Asn Ser Leu Asn Leu Lys Phe Val
                85                  90                  95

Thr Lys Gly Gln Tyr Ser Thr Asn Ile Gly Ser Arg Thr Tyr Leu Met
            100                 105                 110

Glu Ser Asp Thr Lys Tyr Gln Met Phe Gln Leu Leu Gly Asn Glu Phe
        115                 120                 125

Thr Phe Asp Val Asp Val Ser Asn Leu Gly Cys Gly Leu Asn Gly Ala
    130                 135                 140

Leu Tyr Phe Val Ser Met Asp Ala Asp Gly Gly Met Ser Lys Tyr Ser
145                 150                 155                 160

Gly Asn Lys Ala Gly Ala Lys Tyr Gly Thr Gly Tyr Cys Asp Ser Gln
                165                 170                 175

Cys Pro Arg Asp Leu Lys Phe Ile Asn Gly Glu Ala Asn Val Glu Asp
            180                 185                 190

Trp Gln Ser Ser Thr Asn Asp Ala Asn Ala Gly Thr Gly Lys Tyr Gly
        195                 200                 205

Ser Cys Cys Ser Glu Met Asp Val Trp Glu Ala Asn Asn Met Ala Ala
    210                 215                 220

Ala Phe Thr Pro His Pro Cys Thr Val Ile Gly Gln Ser Arg Cys Glu
225                 230                 235                 240

Gly Asp Ser Cys Gly Gly Thr Tyr Ser Thr Asp Arg Tyr Ala Gly Ile
                245                 250                 255

Cys Asp Pro Asp Gly Cys Asp Phe Asn Ser Tyr Arg Gln Gly Asn Lys
            260                 265                 270
```

Thr Phe Tyr Gly Lys Gly Met Thr Val Asp Thr Thr Lys Lys Ile Thr
        275                 280                 285

Val Val Thr Gln Phe Leu Lys Asn Ser Ala Gly Glu Leu Ser Glu Ile
290                 295                 300

Lys Arg Phe Tyr Val Gln Asn Gly Lys Val Ile Pro Asn Ser Glu Ser
305                 310                 315                 320

Thr Ile Pro Gly Val Glu Gly Asn Ser Ile Thr Gln Asp Trp Cys Asp
                325                 330                 335

Arg Gln Lys Ala Ala Phe Gly Asp Val Thr Asp Phe Gln Asp Lys Gly
            340                 345                 350

Gly Met Val Gln Met Gly Lys Ala Leu Ala Gly Pro Met Val Leu Val
        355                 360                 365

Met Ser Ile Trp Asp Asp His Ala Val Asn Met Leu Trp Leu Asp Ser
    370                 375                 380

Thr Trp Pro Ile Asp Gly Ala Gly Lys Pro Gly Ala Glu Arg Gly Ala
385                 390                 395                 400

Cys Pro Thr Thr Ser Gly Val Pro Ala Glu Val Glu Ala Glu Ala Pro
                405                 410                 415

Asn Ser Asn Val Ile Phe Ser Asn Ile Arg Phe Gly Pro Ile Gly Ser
            420                 425                 430

Thr Val Ser Gly Leu Pro Asp Gly Gly Ser Gly Asn Pro Asn Pro Pro
        435                 440                 445

Val Ser Ser Ser Thr Pro Val Pro Ser Ser Ser Thr Thr Ser Ser Gly
    450                 455                 460

Ser Ser Gly Pro Thr Gly Gly Thr Gly Val Ala Lys His Tyr Glu Gln
465                 470                 475                 480

Cys Gly Gly Ile Gly Phe Thr Gly Pro Thr Gln Cys Glu Ser Pro Tyr
                485                 490                 495

Thr Cys Thr Lys Leu Asn Asp Trp Tyr Ser Gln Cys Leu
            500                 505

<210> SEQ ID NO 7
<211> LENGTH: 1648
<212> TYPE: DNA
<213> ORGANISM: Artificial Sequence
<220> FEATURE:
<223> OTHER INFORMATION: Polynucleotide that encodes for the mutant
      Cbh1N209E preprotein of SEQ ID NO: 8

<400> SEQUENCE: 7
atgtacgcca agttcgcgac cctcgccgcc cttgtggctg gcgccgctgc tcagaacgcc    60
tgcactctga ccgctgagaa ccaccccctcg ctgacgtggt ccaagtgcac gtctggcggc   120
agctgcacca cgctccaggg ttccatcacc atcgacgcca actggcggtg gactcaccgg   180
accgatagcg ccaccaactg ctacgagggc aacaagtggg atacttcgta ctgcagcgat   240
ggtccttctt cgcctccaa gtgctgcatc gacggcgctg actactcgag cacctatggc   300
atcaccacga gcggtaactc cctgaacctc aagttcgtca ccaagggcca gtactcgacc   360
aacatcggct cgcgtaccta cctgatggag agcgacacca gtaccagag taagttcctc   420 tcgcaccccg ccgccgggag atgatggcgc ccagcccgct gacgcgaatg acacagtgtt   480
ccagctcctc ggcaacgagt tcaccttcga tgtcgacgtc tccaacctcg ctgcggcct    540 caatggcgcc ctctacttcg tgtccatgga tgccgatggt ggcatgtcca agtactcggg   600
caacaaggca ggtgccaagt acggtaccgg ctactgtgat tctcagtgcc cccgcgacct   660

```
caagttcatc aacggcgagg ccaacgtaga ggagtggcag agctcgacca acgatgccaa    720
cgccggcacg ggcaagtacg gcagctgctg ctccgagatg gacgtctggg aggccaacaa    780
catggccgcc gccttcactc cccacccttg caccgtgatc ggccagtcgc gctgcgaggg    840
cgactcgtgc ggcggtacct acagcaccga ccgctatgcc ggcatctgcg accccgacgg    900
atgcgacttc aactcgtacc gccagggcaa caagaccttc tacggcaagg gcatgacggt    960
cgacacgacc aagaagatca cggtcgtcac ccagttcctc aagaactcgg ccggcgagct   1020
ctccgagatc aagcggttct acgtccagaa cggcaaggtc atccccaact ccgagtccac   1080
catcccgggc gtcgagggca actccatcac ccaggactgg tgcgaccgcc agaaggccgc   1140
cttcggcgac gtgaccgact ccaggacaa gggcggcatg gtccagatgg gcaaggccct   1200
cgcggggccc atggtcctcg tcatgtccat ctgggacgac cacgccgtca acatgctctg   1260
gctcgactcc acctggccca tcgacggcgc cggcaagccg ggcgccgagc gcggtgcctg   1320
ccccaccacc tcgggcgtcc ccgctgaggt cgaggccgag gccccaact ccaacgtcat   1380 cttctccaac atccgcttcg gccccatcgg ctccaccgtc tccggcctgc cgacggcgg   1440 cagcggcaac cccaacccgc ccgtcagctc gtccaccccg gtccctcct cgtccaccac   1500 atcctccggt tcctccggcc cgactggcgg cacgggtgtc gctaagcact atgagcaatg   1560
cggaggaatc gggttcactg gcctacccca gtgcgagagc ccctacactt gcaccaagct   1620
gaatgactgg tactcgcagt gcctgtaa                                     1648
```

<210> SEQ ID NO 8
<211> LENGTH: 526
<212> TYPE: PRT
<213> ORGANISM: Artificial Sequence
<220> FEATURE:
<223> OTHER INFORMATION: Preprotein of the Cbh1 mutant Cbh1N209E
<220> FEATURE:
<221> NAME/KEY: SIGNAL
<222> LOCATION: (1)..(17)

<400> SEQUENCE: 8

```
Met Tyr Ala Lys Phe Ala Thr Leu Ala Ala Leu Val Ala Gly Ala Ala
1               5                   10                  15

Ala Gln Asn Ala Cys Thr Leu Thr Ala Glu Asn His Pro Ser Leu Thr
                20                  25                  30

Trp Ser Lys Cys Thr Ser Gly Gly Ser Cys Thr Ser Val Gln Gly Ser
            35                  40                  45

Ile Thr Ile Asp Ala Asn Trp Arg Trp Thr His Arg Thr Asp Ser Ala
        50                  55                  60

Thr Asn Cys Tyr Glu Gly Asn Lys Trp Asp Thr Ser Tyr Cys Ser Asp
65                  70                  75                  80

Gly Pro Ser Cys Ala Ser Lys Cys Cys Ile Asp Gly Ala Asp Tyr Ser
                85                  90                  95

Ser Thr Tyr Gly Ile Thr Thr Ser Gly Asn Ser Leu Asn Leu Lys Phe
            100                 105                 110

Val Thr Lys Gly Gln Tyr Ser Thr Asn Ile Gly Ser Arg Thr Tyr Leu
        115                 120                 125

Met Glu Ser Asp Thr Lys Tyr Gln Met Phe Gln Leu Leu Gly Asn Glu
    130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Ala Asp Gly Gly Met Ser Lys Tyr
                165                 170                 175
```

Ser Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Val Glu
        195                 200                 205

Glu Trp Gln Ser Ser Thr Asn Asp Ala Asn Ala Gly Thr Gly Lys Tyr
    210                 215                 220

Gly Ser Cys Cys Ser Glu Met Asp Val Trp Glu Ala Asn Asn Met Ala
225                 230                 235                 240

Ala Ala Phe Thr Pro His Pro Cys Thr Val Ile Gly Gln Ser Arg Cys
                245                 250                 255

Glu Gly Asp Ser Cys Gly Gly Thr Tyr Ser Thr Asp Arg Tyr Ala Gly
            260                 265                 270

Ile Cys Asp Pro Asp Gly Cys Asp Phe Asn Ser Tyr Arg Gln Gly Asn
        275                 280                 285

Lys Thr Phe Tyr Gly Lys Gly Met Thr Val Asp Thr Thr Lys Lys Ile
    290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Glu Gly Asn Ser Ile Thr Gln Asp Trp Cys
            340                 345                 350

Asp Arg Gln Lys Ala Ala Phe Gly Asp Val Thr Asp Phe Gln Asp Lys
        355                 360                 365

Gly Gly Met Val Gln Met Gly Lys Ala Leu Ala Gly Pro Met Val Leu
    370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                405                 410                 415

Ala Cys Pro Thr Thr Ser Gly Val Pro Ala Glu Val Glu Ala Glu Ala
            420                 425                 430

Pro Asn Ser Asn Val Ile Phe Ser Asn Ile Arg Phe Gly Pro Ile Gly
        435                 440                 445

Ser Thr Val Ser Gly Leu Pro Asp Gly Ser Gly Asn Pro Asn Pro
    450                 455                 460

Pro Val Ser Ser Ser Thr Pro Val Pro Ser Ser Ser Thr Ser Ser
465                 470                 475                 480

Gly Ser Ser Gly Pro Thr Gly Gly Thr Val Ala Lys His Tyr Glu
                485                 490                 495

Gln Cys Gly Gly Ile Gly Phe Thr Gly Pro Thr Gln Cys Glu Ser Pro
            500                 505                 510

Tyr Thr Cys Thr Lys Leu Asn Asp Trp Tyr Ser Gln Cys Leu
        515                 520                 525

<210> SEQ ID NO 9
<211> LENGTH: 509
<212> TYPE: PRT
<213> ORGANISM: Artificial Sequence
<220> FEATURE:
<223> OTHER INFORMATION: Mature protein Cbh1N209E

<400> SEQUENCE: 9

Gln Asn Ala Cys Thr Leu Thr Ala Glu Asn His Pro Ser Leu Thr Trp
1               5                   10                  15

```
Ser Lys Cys Thr Ser Gly Gly Ser Cys Thr Ser Val Gln Gly Ser Ile
        20                  25                  30

Thr Ile Asp Ala Asn Trp Arg Trp Thr His Arg Thr Asp Ser Ala Thr
        35                  40                  45

Asn Cys Tyr Glu Gly Asn Lys Trp Asp Thr Ser Tyr Cys Ser Asp Gly
50                  55                  60

Pro Ser Cys Ala Ser Lys Cys Ile Asp Gly Ala Asp Tyr Ser Ser
65                  70                  75                  80

Thr Tyr Gly Ile Thr Thr Ser Gly Asn Ser Leu Asn Leu Lys Phe Val
            85                  90                  95

Thr Lys Gly Gln Tyr Ser Thr Asn Ile Gly Ser Arg Thr Tyr Leu Met
            100                 105                 110

Glu Ser Asp Thr Lys Tyr Gln Met Phe Gln Leu Leu Gly Asn Glu Phe
            115                 120                 125

Thr Phe Asp Val Asp Val Ser Asn Leu Gly Cys Gly Leu Asn Gly Ala
        130                 135                 140

Leu Tyr Phe Val Ser Met Asp Ala Asp Gly Gly Met Ser Lys Tyr Ser
145                 150                 155                 160

Gly Asn Lys Ala Gly Ala Lys Tyr Gly Thr Gly Tyr Cys Asp Ser Gln
                165                 170                 175

Cys Pro Arg Asp Leu Lys Phe Ile Asn Gly Glu Ala Asn Val Glu Glu
            180                 185                 190

Trp Gln Ser Ser Thr Asn Asp Ala Asn Ala Gly Thr Gly Lys Tyr Gly
            195                 200                 205

Ser Cys Cys Ser Glu Met Asp Val Trp Glu Ala Asn Asn Met Ala Ala
210                 215                 220

Ala Phe Thr Pro His Pro Cys Thr Val Ile Gly Gln Ser Arg Cys Glu
225                 230                 235                 240

Gly Asp Ser Cys Gly Gly Thr Tyr Ser Thr Asp Arg Tyr Ala Gly Ile
                245                 250                 255

Cys Asp Pro Asp Gly Cys Asp Phe Asn Ser Tyr Arg Gln Gly Asn Lys
            260                 265                 270

Thr Phe Tyr Gly Lys Gly Met Thr Val Asp Thr Lys Lys Ile Thr
            275                 280                 285

Val Val Thr Gln Phe Leu Lys Asn Ser Ala Gly Glu Leu Ser Glu Ile
290                 295                 300

Lys Arg Phe Tyr Val Gln Asn Gly Lys Val Ile Pro Asn Ser Glu Ser
305                 310                 315                 320

Thr Ile Pro Gly Val Glu Gly Asn Ser Ile Thr Gln Asp Trp Cys Asp
                325                 330                 335

Arg Gln Lys Ala Ala Phe Gly Asp Val Thr Asp Phe Gln Asp Lys Gly
            340                 345                 350

Gly Met Val Gln Met Gly Lys Ala Leu Ala Gly Pro Met Val Leu Val
            355                 360                 365

Met Ser Ile Trp Asp Asp His Ala Val Asn Met Leu Trp Leu Asp Ser
            370                 375                 380

Thr Trp Pro Ile Asp Gly Ala Gly Lys Pro Gly Ala Glu Arg Gly Ala
385                 390                 395                 400

Cys Pro Thr Thr Ser Gly Val Pro Ala Glu Val Glu Ala Glu Ala Pro
                405                 410                 415

Asn Ser Asn Val Ile Phe Ser Asn Ile Arg Phe Gly Pro Ile Gly Ser
            420                 425                 430
```

Thr Val Ser Gly Leu Pro Asp Gly Gly Ser Gly Asn Pro Asn Pro Pro
        435                 440                 445

Val Ser Ser Ser Thr Pro Val Pro Ser Ser Thr Thr Ser Ser Gly
    450                 455                 460

Ser Ser Gly Pro Thr Gly Gly Thr Gly Val Ala Lys His Tyr Glu Gln
465                 470                 475                 480

Cys Gly Gly Ile Gly Phe Thr Gly Pro Thr Gln Cys Glu Ser Pro Tyr
                485                 490                 495

Thr Cys Thr Lys Leu Asn Asp Trp Tyr Ser Gln Cys Leu
        500                 505

<210> SEQ ID NO 10
<211> LENGTH: 52
<212> TYPE: DNA
<213> ORGANISM: Artificial Sequence
<220> FEATURE:
<223> OTHER INFORMATION: Oligonucleotide 1

<400> SEQUENCE: 10
ccgcggtggc ggccgctcta gacgctgcac tgtggcacga ctaccagtga tc          52

<210> SEQ ID NO 11
<211> LENGTH: 52
<212> TYPE: DNA
<213> ORGANISM: Artificial Sequence
<220> FEATURE:
<223> OTHER INFORMATION: Oligonucleotide 2

<400> SEQUENCE: 11
gctgcagccc gggggatccc caggctaatt gtcgcgtcgc ttcggacgga ca          52

<210> SEQ ID NO 12
<211> LENGTH: 52
<212> TYPE: DNA
<213> ORGANISM: Artificial Sequence
<220> FEATURE:
<223> OTHER INFORMATION: Oligonucleotide 3

<400> SEQUENCE: 12
catggtcata gaattcgata tcaacctctc tgaaggaggt tctgagacac gc          52

<210> SEQ ID NO 13
<211> LENGTH: 60
<212> TYPE: DNA
<213> ORGANISM: Artificial Sequence
<220> FEATURE:
<223> OTHER INFORMATION: Oligonucleotide 4

<400> SEQUENCE: 13
tgggtaccgg gccccccctc gagctagaag aagggcgtaa ataagaagct ataatagctt    60

<210> SEQ ID NO 14
<211> LENGTH: 22
<212> TYPE: DNA
<213> ORGANISM: Artificial Sequence
<220> FEATURE:
<223> OTHER INFORMATION: Oligonucleotide 5

<400> SEQUENCE: 14
aacaagtggg atacttcgta ct                                            22

<210> SEQ ID NO 15
<211> LENGTH: 21
<212> TYPE: DNA

```
<213> ORGANISM: Artificial Sequence
<220> FEATURE:
<223> OTHER INFORMATION: Oligonucleotide 6

<400> SEQUENCE: 15
atccatggac acgaagtaga g                                             21

<210> SEQ ID NO 16
<211> LENGTH: 33
<212> TYPE: DNA
<213> ORGANISM: Artificial Sequence
<220> FEATURE:
<223> OTHER INFORMATION: Oligonucleotide 7

<400> SEQUENCE: 16
ccgacatatg aagcagtacc tccagtacct cgc                                33

<210> SEQ ID NO 17
<211> LENGTH: 35
<212> TYPE: DNA
<213> ORGANISM: Artificial Sequence
<220> FEATURE:
<223> OTHER INFORMATION: Oligonucleotide 8

<400> SEQUENCE: 17
gctgaattct tagacgttga cagtcgagcc gatgg                              35

<210> SEQ ID NO 18
<211> LENGTH: 26
<212> TYPE: DNA
<213> ORGANISM: Artificial Sequence
<220> FEATURE:
<223> OTHER INFORMATION: Oligonucleotide 9

<400> SEQUENCE: 18
gtgctgatcc tcttccgtcc catatg                                        26

<210> SEQ ID NO 19
<211> LENGTH: 24
<212> TYPE: DNA
<213> ORGANISM: Artificial Sequence
<220> FEATURE:
<223> OTHER INFORMATION: Oligonucleotide 10

<400> SEQUENCE: 19
ctcgaggtcg acggtatcga taag                                          24
```

VARIANTS OF CELLOBIOHYDROLASE 1

INCORPORATION BY REFERENCE OF SEQUENCE LISTING

A sequence listing created on Jan. 23, 2018 as the ASCII text file "SeqList_03504_006224-USO" having a file size of 36,500 bytes, is incorporated herein by reference in its entirety.

The invention belongs to the field of enzymes useful for hydrolysis processes of cellulosic biomass during production of bioproducts, more particularly, to variants of the cellobiohydrolase 1 enzyme and their use in the production of fermentable sugars and ethanol from cellulosic material.

PRIOR ART

Biofuels are an attractive alternative to fossil fuels and can be obtained by fermentation of monomeric sugars derived from starch or cellulose and hemicellulose.

Plant biomass provides a comprehensive source of potential energy in the form of sugars that can be used for many industrial and agricultural processes, and is therefore a significant renewable resource for the generation of fermentable sugars that can give rise to commercially valuable end products such as biofuels. However, the enormous potential energy of these carbohydrates is currently underused because sugars are part of complex polymers that are not readily accessible for fermentation.

Any plant biomass can be considered a raw material for the production of biofuels such as arable crops, other agricultural waste or even municipal solid waste. These materials mainly comprise cellulose and hemicellulose. Once the cellulose and hemicellulose are converted to glucose and xylose, respectively, by means of an enzymatic hydrolysis process, these compounds are easily fermented into ethanol by other organisms. Thus, the greater the amount of complex sugars remains at the end of hydrolytic process, the lower the yield of ethanol production at the end of the fermentation process. Therefore, an area of research intended for reducing costs and enhancing the performance of biofuel production procedures focuses on improving the efficiency of cellulolytic enzymes, as well as the enzyme cocktails comprising said enzymes and that can be used to generate fermentable sugars from biomass.

Due to the complexity of biomass, its conversion to monomeric sugars involves the action of various types of enzymes with various enzyme activities that digest cellulose, hemicellulose and other complex polymers present in the biomass. After cellulose, hemicellulose is the most abundant naturally occurring fraction. Both cellulose and hemicellulose can be previously treated mechanically, chemically, enzymatically or by other means to increase their susceptibility to hydrolysis. After this pretreatment process, a saccharification stage takes place, which is an enzyme process whereby complex carbohydrates are degraded into their monosaccharide components. The goal of any saccharification technology is to alter or eliminate structural and compositional impediments for hydrolysis in order to improve the rate of enzyme hydrolysis and increase the yields of fermentable sugars from biomass, which comprises mainly cellulose and hemicellulose (Mosier N. et al., 2005, Bioresource Technology 96, 673-686). After this saccharification stage, a fermentation process is performed.

Individual enzymes have shown to digest only partially cellulose and hemicellulose and, therefore, the concerted action of all or at least several of the enzymes called "cellulases or cellulolytic enzymes" is required to complete the conversion of the different complex polymers, specifically cellulose and hemicellulose, to monomeric sugars. Cellulases (1,4-beta-D-glucan-4-glucanohydrolase, E.C. 3.2.1.4) comprise at least three enzyme activities, endo-beta-glucanases (E.C. 3.2.1.4), exo-beta-glucanases or cellobiohydrolases (E.C. 3.2.1.91) and beta-glucosidases (E.C. 3.2.1.21), the synergetic action of which has been shown in the hydrolysis of cellulose (Woodward, J. 1991, Bioresource Technology Vol 36, 67-75). Besides these three activities, nowadays other equally important activities, such as xylanases (E.C. 3.2.1.8), beta-xylosidases (E.C. 3.2.1.37) and polysaccharide monooxygenases (also called PMO, AA9, glycosyl hydrolases of the 61 family or GH61), are also known.

The hydrolytic effectiveness of a multienzyme complex-composed of a wide variety of cellulolytic enzymes—in the cellulosic saccharification process depends both on the properties of the individual enzymes and on the relationship of each enzyme in the complex.

Microbial cellulases have become the centre of attention as enzyme biocatalysts because of their complex nature and their extensive industrial applications. Today considerable attention is paid to current knowledge on the production of cellulases and challenges in research on cellulases, especially in the direction of improving the economy of various industrial processes, in order to obtain cellulases with greater activity and improved properties.

Specifically, the cellobiohydrolase is an enzyme that catalyzes the hydrolysis of cellulose into cellobiose by means of exoglucanase activity, sequentially releasing cellobiose molecules from the ends, reducing or not, of the cellulose or cellooligosaccharides, thereby leaving the cellobiose accessible to continue being hydrolyzed to glucose by betaglucosidases. Therefore, it is widely used together with other cellulases in processes for converting cellulosic biomass into fermentable sugars.

Two types of cellobiohydrolases, cellobiohydrolase 1 (Cbh1 or Cbh1a) and cellobiohydrolase 2 (Cbh2 or Cbh1Ia), have been described. The former hydrolyzes from the reducing end of the cellulose chain. The second hydrolyzes from the nonreducing end of the cellulose chain.

According to the above, there is a need to develop new and improved cellobiohydrolases with greater productivity that maintain their hydrolytic capacity during the course of the saccharification process, for use in the conversion of cellulose to fermentable sugars. In this regard, cellobiohydrolases with improved hydrolytic activity due to their lower inhibition per product have been designed (WO2012048171A2, WO2012051055A2).

It would therefore be useful to have a cellobiohydrolase with improved cellulolytic activity, capable of producing fermentable sugars more efficiently, thereby improving the overall hydrolytic yield of the enzyme mixtures containing it.

DESCRIPTION OF THE INVENTION

The present invention describes variants of the cellobiohydrolase 1 enzyme (Cbh1), the use of these variants for the hydrolysis of cellulosic material to fermentable sugars and a process for producing fermentable sugars and a process for producing bioproducts, such as ethanol, wherein said variants are used.

Therefore, the present invention represents a solution to the need to provide cellobiohydrolase variants with improved cellulolytic activity, useful for optimising the stage of hydrolysis of cellulosic material to fermentable sugars.

The inventors have shown that the cellobiohydrolase variants of the present invention have greater cellulolytic activity than the parental cellobiohydrolase from which they were obtained. Thus, these variants make it possible to obtain a larger amount of glucose released at the end of hydrolytic process by the enzyme cocktails that comprise them, compared to the same cocktails comprising, instead of the variant of the invention, parental cellobiohydrolase (native). Therefore, their use within such enzyme compositions significantly increases the yield of the hydrolysis stage upon increasing the monosaccharide sugars released at the end of hydrolysis (essentially glucose), thereby increasing production of the final bioproduct, preferably ethanol.

As shown in the examples described below, variants of Cbh1 of the present invention were expressed in a fungal host cell and the enzyme mixture produced by the resulting strain was evaluated in saccharification experiments of pretreated biomass (PCS), verifying an increase in the performance of the saccharification process, namely an increase in the concentration of fermentable sugars (glucose) released at the end of the process, compared with the same enzyme mixture produced by the untransformed control strain (FIGS. 10 and 17).

Therefore, a first aspect of the present invention relates to an isolated variant of cellobiohydrolase 1 (Cbh1 or Cbh1a) comprising an amino acid sequence having a sequence identity of at least 80%, 85%, 90%, 91%, 92%, 93%, 94%, 95%, 96%, 97%, 98% or 99% with SEQ ID NO: 2 and comprises an amino acid substitution in position N209 corresponding to positions 1 to 526 of SEQ ID NO: 2, wherein said substitution is by an acidic amino acid and wherein the Cbh1 variant has greater cellobiohydrolase activity compared to the native Cbh1 consisting of SEQ ID NO: 3. Hereinafter, this variant shall be called "Cbh1 variant of the invention".

The "greater cellobiohydrolase activity" in comparison with the native Cbh1 is measured, preferably, by testing glucose release from lignocellulosic biomass treated with an enzyme mixture comprising the Cbh1 variant of the invention against the same enzyme mixture that does not comprise this enzyme, but rather the native Cbh1 consisting of SEQ ID NO: 3 and under the same hydrolysis conditions. Preferably, these tests are carried out as explained later in the examples shown below, i.e. in the presence of the Avicel substrate (microcrystalline cellulose, which is a commercially available product) or corn stover, preferably pretreated with dilute acid and steam explosion as the starting lignocellulosic biomass and in the presence of an enzyme cocktail secreted by the *Myceliophthora thermophila* C1 strain.

The term "variant", as used herein, refers to an enzyme derived from a native enzyme by means of one or more deletions, insertions and/or substitutions of one or more amino acids and therefore has a different sequence to that of the native enzyme. As used herein, the expression "Cbh1 variant" means a polypeptide having cellobiohydrolase activity produced, preferably, by an organism expressing a nucleotide sequence coding for a native Cbh1 which has been modified to encode said Cbh1 variant. Said modified nucleotide sequence is obtained through human intervention by modifying the nucleotide sequence that encodes a native Cbh1. The term "modification" herein means any chemical modification of the amino acid or nucleic acid sequence of a native Cbh1.

The term "native Cbh1" refers to a Cbh1 enzyme or its preprotein, expressed by a microorganism with its natural unmodified sequence. Preferably, the native Cbh1 enzyme, to which reference is made herein, is expressed by a filamentous fungus, more preferably a fungus belonging to the genus *Myceliophthora*, even more preferably by *Myceliophthora thermophila*, even more preferably the native Cbh1 enzyme is the enzyme of SEQ ID NO: 2 or SEQ ID NO: 3. SEQ ID NO: 2 is the preprotein of SEQ ID NO: 3 and contains a signal peptide corresponding to amino acids 1 to 17 of SEQ ID NO: 2 linked to SEQ ID NO: 3.

The Cbh1 variants of the invention may be derived either from a library of mutants or can be designed by means of any procedure known to the persons skilled in the art to generate a library of mutants of an enzyme. The mutants that constitute said library may comprise substitutions, deletions and/or insertions of one or more amino acids in their amino acid sequences.

The amino acid substitution at position N209, corresponding to positions 1 to 526 of SEQ ID NO: 2, is by an amino acid with acidic properties, for example, Aspartic Acid, D or Glutamic Acid, E. Therefore, the substitution of Asparagine at position N209, corresponding to positions 1 to 526 of SEQ ID NO: 2, is by amino acids having the same properties over, for example, acidity, hydrophobicity or aromaticity properties as amino acid E (Glutamic acid), for example Aspartic Acid (D).

"Acidic amino acid" is understood to be amino acids with side chains of an acidic nature, negatively charged at physiological pH.

The amino acid substitution of the variant of the invention in the Asparagine of position 209 (N209) of SEQ ID NO: 2 is by an acidic amino acid, preferably, by Aspartic (D) or Glutamic acid (E), more preferably Glutamic. Thus, a preferred embodiment relates to the Cbh1 variant of the invention, wherein the amino acid substitution is N209D or N209E. Substitutions in N209 by other acidic amino acids different from D and E must allow the Cbh1 variants of the invention to maintain the same function as the preferred variants of N209D and N209E, including the improvement of their cellobiohydrolase activity compared to the native Cbh1 that comprises an N at position 209 corresponding to SEQ ID NO: 2.

The term "identity", as used herein, in the context of describing two or more polypeptide sequences, makes reference to a specified percentage of amino acid residue matches at positions from an alignment of two amino acid sequences. Sequence alignment procedures for comparison are well known in the art. The degree of identity may be determined by the Clustal Method (Higgins, 1989, CABIOS 5: 151-153), the Wilbur-Lipman Method (Wilbur and Lipman, 1983, *Proceedings of the National Academy of Science USA* 80: 726-730), GAG Program, including GAP (Devereux et al. 1984, *Nucleic Acids Research* 12: 287 Genetics Computer Group University of Wisconsin, Madison, (Wis.)); BLAST or BLASTN, EMBOSS Needle and FASTA (Altschul et al. 1999, *J. Mol. Biol.* 215: 403-410). Furthermore, the Smith-Waterman Algorithm can be used to determine the degree of identity between two sequences.

For sequence comparison, typically one sequence acts as a reference sequence against to which the "problem" sequences are compared. When a sequence comparison algorithm is used to determine their identity, the reference sequence and the problem sequence(s) is/are introduced in the program, and its parameters are configured. The program parameters that appear by default can be used or they may be configured, preferably said parameters will be those displayed by default. Thus, the sequence comparison algorithm calculates the identity percentage between the problem sequence(s) and the reference sequence based on the program's parameters. Two examples of algorithms that are useful for determining percent sequence identity are BLAST and BLAST 2.0, described in Altschul et al. (1997) *Nucleic Acids Res* 25(17):3389-3402 and Altschul et al. (1990) *J. Mol Biol* 215(3)-403-410, respectively. Preferably, the degree of identify to which this invention relates is calculated by means of BLAST. The BLAST analysis software is available to the public at the National Center for Biotechnology Information (NCBI).

The Cbh1 variant of the invention may exhibit limited changes in its amino acid sequence. These changes must make it possible to maintain the cellobiohydrolase activity of the preferred Cbh1 variant of the invention (which comprises SEQ ID NO: 6 or SEQ ID NO: 9) compared to the native Cbh1. These changes may be substitutions, deletions and/or additions. Substitutions are for conserved amino acids that are amino acids with side chains and similar properties with regard to, for example, hydrophobic or aromatic properties. These substitutions include, but are not limited to, substitutions between Glu and Asp, Lys and Arg, Asn and Gln, Ser and Thr, and/or among the amino acids included in the following list: Ala, Leu, Val and Ile. The changes do not lead to significant changes in the essential characteristics or properties of the Cbh1 variant of the invention.

In a more preferred embodiment, the Cbh1 variant of the invention comprises the amino acid sequence SEQ ID NO: 6 or SEQ ID NO: 9. An example of the Cbh1 variant of the invention that comprises the amino acid sequence SEQ ID NO: 6 is the polypeptide of SEQ ID NO: 5, which is the preprotein of SEQ ID NO: 6, which consists of a signal peptide corresponding to amino acids 1 to 17 of SEQ ID NO: 5 linked to SEQ ID NO: 6. An example of the Cbh1 variant of the invention that comprises the amino acid sequence SEQ ID NO: 9 is the polypeptide of SEQ ID NO: 8, which is the preprotein of SEQ ID NO: 9, which consists of a signal peptide corresponding to amino acids 1 to 17 of SEQ ID NO: 8 linked to SEQ ID NO: 9. Thus, in a more preferred embodiment, the Cbh1 variant of the invention consists of amino acid sequence SEQ ID NO: 6 or SEQ ID NO: 9. This SEQ ID NO: 6 corresponds to the mature Cbh1 (without the signal peptide) of SEQ ID NO: 5. Said sequence SEQ ID NO: 6 shall hereinafter also be called the mature protein of Cbh1N209D. SEQ ID NO: 9 corresponds to the mature Cbh1 (without the signal peptide) of SEQ ID NO: 8. Said sequence SEQ ID NO: 9 shall hereinafter also be called the mature protein of Cbh1N209E.

In a more preferred embodiment, the Cbh1 variant of the invention consists of the amino acid sequence SEQ ID NO: 5 or SEQ ID NO: 8. This SEQ ID NO: 5 corresponds to the native Cbh1 of SEQ ID NO: 2 which comprises the substitution of amino acid N209D. As shown in the examples below, the N209D replacement increases the hydrolytic activity of Cbh1 throughout the saccharification process, thereby increasing the final concentration of fermentable sugars in the hydrolytic process from cellulosic material. Said sequence SEQ ID NO: 5 shall hereinafter also be called Cbh1N209D preprotein. SEQ ID NO: 8 corresponds to the native Cbh1 of SEQ ID NO: 2 which comprises the substitution of amino acid N209E. As shown in the examples below, the N209E replacement increases the hydrolytic activity of Cbh1 throughout the saccharification process, thereby increasing the final concentration of fermentable sugars in the hydrolytic process from cellulosic material. Said sequence SEQ ID NO: 8 shall hereinafter also be called Cbh1N209E preprotein.

The term "preprotein" refers to a polypeptide including a signal peptide (or leader sequence) at its amino terminal end. Said signal peptide is cleaved from the preprotein by a peptidase, thereby secreting the mature protein. The secreted polypeptide portion is called "mature protein" or "secreted protein". The "signal peptide" is that which directs the polypeptide within the cell towards its secretion pathway.

The Cbh1 variant of the invention can be synthesised, for example, but not limited to, in vitro. For example, by means of peptide synthesis in solid phase or recombinant DNA approaches. The Cbh1 variant of the invention may be produced recombinantly, including its production as a mature peptide or as a preprotein that includes a signal peptide.

The Cbh1 variant of the invention may be prepared by any means known in the art, such as modification of a DNA sequence that encodes a native Cbh1, such as, for example, but not limited to, SEQ ID NO: 1, that encodes the preprotein of SEQ ID NO: 2, transformation of the modified DNA sequence in a suitable host cell and expression of the modified DNA sequence to obtain the enzyme variant.

Due to the degeneration of the genetic code, various nucleotide sequences can encode the same amino acid sequence. Therefore, in another aspect, the invention provides an isolated nucleic acid sequence that encodes the Cbh1 variant of the invention, hereinafter "nucleic acid sequence of the invention", and the nucleic acid sequence complementary thereto.

According to the present invention, an "isolated nucleic acid molecule", "nucleotide sequence", "nucleic acid sequence" or "polynucleotide" is a nucleic acid molecule (polynucleotide) which has been removed from its natural environment (i.e. which has been subjected to human manipulation) and may include DNA, RNA, or DNA or RNA derivatives, including cDNA. The nucleotide sequence of the present invention may or may not be chemically or biochemically modified and can be artificially obtained by cloning, amplification and selection or synthesis procedures. The nucleic acid sequence of the invention can encode the mature polypeptide or a preprotein consisting of a signal peptide attached to the mature enzyme that must be processed later.

The nucleotide sequence of the present invention may also comprise other elements such as introns, noncoding sequences at the 3 'and/or 5' ends, ribosome binding sites, etc. This nucleotide sequence may also include encoding sequences for additional amino acids which are useful for the purification or stability of the encoded peptide.

In a preferred embodiment, the nucleic acid sequence of the invention is SEQ ID NO: 4, which is the nucleic acid sequence that encodes the amino acid sequence SEQ ID NO: 5 (preprotein of SEQ ID NO: 6). In another preferred embodiment, the nucleic acid sequence of the invention is SEQ ID NO: 7, which is the nucleic acid sequence that encodes the amino acid sequence SEQ ID NO: 8 (preprotein of SEQ ID NO: 9).

The expression "complementary nucleic acid sequence" of a nucleic acid sequence that encodes the Cbh1 variant of the invention makes reference to the nucleic acid sequence of the strand complementary to which the Cbh1 variant of the invention encodes. It shall be appreciated that a double-stranded DNA which encodes a given amino acid sequence comprises a single-stranded DNA and its complementary strand, which has a sequence that is complementary to the single-stranded DNA.

Table 1 shows a detailed description of some of the sequences mentioned throughout the present invention.

TABLE 1

Description of some of the sequences mentioned in the present invention.

| Sequence | DESCRIPTION |
|---|---|
| SEQ ID NO: 1 | Polynucleotide that encodes for the native Cbh1 preprotein |
| SEQ ID NO: 2 | Preprotein of the native Cbh1 (includes the 17 amino acids corresponding to the signal peptide) |
| SEQ ID NO: 3 | Mature native Cbh1 protein |
| SEQ ID NO: 4 | Polynucleotide that encodes for the mutant Cbh1N209D preprotein |
| SEQ ID NO: 5 | Preprotein of the Cbh1 mutant Cbh1N209D (includes the 17 amino acids corresponding to the signal peptide) |
| SEQ ID NO: 6 | Mature protein Cbh1N209D |
| SEQ ID NO: 7 | Polynucleotide that encodes for the mutant Cbh1N209E preprotein |
| SEQ ID NO: 8 | Preprotein of the Cbh1 mutant Cbh1N209E (includes the 17 amino acids corresponding to the signal peptide) |
| SEQ ID NO: 9 | Mature protein Cbh1N209E |

The nucleic acid sequence of the invention can be included in a genetic construct, preferably an expression vector. Said genetic construct may also comprise one or more regulatory sequences of the gene expression, such as promoters, terminators, etc. Therefore, in another aspect, the invention provides a genetic construct that comprises the nucleic acid sequence of the invention or the nucleic acid sequence complementary thereto, hereinafter the "genetic construct of the invention." In a preferred embodiment, said genetic construct is an expression vector.

The expression "genetic construct" or "nucleic acid construct" as used herein makes reference to a necessary functional unit for the transfer or expression of a gene of interest, herein, the nucleic acid sequence of the invention as it has been described, and regulatory sequences, including, for example, a promoter, operatively linked to the sequence that encodes the protein. It refers to a double-stranded nucleic acid molecule which is isolated from a natural nucleic acid or artificially modified to contain nucleic acid segments. The expression nucleic acid construct is synonymous with the expression "expression cassette", when the nucleic acid construct contains the control sequences required for expression of the encoding sequence.

The term "expression vector", also known as "expression construct" or "plasmid", makes reference to a DNA molecule, linear or circular, that comprises the nucleic acid sequence of the invention and which is operatively linked to additional segments that enable the transcription of the encoded peptide. Generally, a plasmid is used to introduce a specific gene in a target cell. Once the expression vector is inside the cell, the protein that is encoded by the gene is produced by the ribosomal complexes of the cellular transcription and translation machinery. The plasmid is frequently subjected to genetic engineering in order to contain regulatory sequences which act as enhancer and promoter regions and which lead to the efficient transcription of the gene ported in the expression vector. The objective of a properly designed vector expression is to produce large amounts of stable messenger RNA and, therefore, proteins. Expression vectors are basic tools of biotechnology and protein production, such as enzymes. The expression vector of the invention is introduced into a host cell such that the vector is maintained as a chromosomal member or as a self-replicating extrachromosomal vector.

Examples of expression vectors are phages, cosmids, phagemids, yeast artificial chromosomes (YAC), bacterial artificial chromosomes (BAC), human artificial chromosomes (HAC) or viral vectors such as adenovirus, retrovirus or lentivirus.

The genetic constructs of the present invention encompass an expression vector, wherein the expression vector can be used to transform a suitable host or hosting cell for the host to express the Cbh1 variant of the invention. The procedures for the recombinant expression of proteins in fungi and other organisms are well known in the art and there are numerous expression vectors or they can be constructed using routine procedures.

The expression "control sequences" is defined herein to include all components which are necessary or advantageous for the expression of the nucleic acid sequence of the present invention. Such control sequences include, but are not limited to, a leader, a polyadenylation sequence, a propeptide sequence, a promoter, a signal peptide sequence and a transcription terminator. The control sequences include at least a promoter and transcription and translation termination signals. The control sequences may be provided with linkers for the purpose of introducing specific restriction sites that facilitate binding of the control sequences with the coding region of the nucleic acid sequence of the present invention. The expression "operatively linked" herein indicates a configuration in which a control sequence is placed in a suitable position regarding the nucleic acid sequence of the present invention, in such a way that the control sequence directs the expression of the nucleic acid sequence of the present invention.

The expression vector of the invention may be an autonomously replicating vector, i.e. a vector that exists as an extrachromosomal entity, the replication of which is independent from chromosomal replication, for example a plasmid, an extrachromosomal element, a minichromosome or an artificial chromosome. The vector may contain any means to guarantee self-replication. Alternatively, the vector may be one which, when introduced into the host cell, is integrated into the genome and replicated together with the chromosome(s) in which has been integrated.

Additionally, a single vector or plasmid or two or more vectors or plasmids may be used, which jointly contain the total DNA to be introduced into the genome of the host cell, or a transposon.

The vectors used in the present invention preferably contain one or more selectable markers that enable the easy selection of the transformed, transfected, transduced or similar, cells. A selectable marker is a gene product that provides resistance to a biocide or a virus, to heavy metals, prototrophy to auxotrophs and similar. The selectable markers for use in a host cell of a filamentous fungus include, but are not limited to, AmdS (acetamidase), ArgB (ornithine carbamoyltransferase), Bar (phosphinothricin acetyltransferase), Hph (hygromycin phosphotransferase), NiaD (nitrate reductase), PyrG (orotidine 5'-phosphate decarboxylase), CysC (sulfate adenyltransferase) and TrpC (anthranilate synthase), in addition to equivalents thereof.

The vectors used in the present invention contain, preferably, one or more elements that enable the integration of the vector in the genome of the host cell or the autonomous replication of the vector in the cell regardless of the genome. For integration in the genome of the host cell, the vector may rely on the nucleic acid sequence of the present invention or any other element of the vector for integration in the genome by means of homologous or non-homologous recombination. Alternatively, the vector may contain additional nucleotide sequences for directing the integration by homologous recombination into the genome of the host cell in one or more precise location(s) in the chromosome(s).

For autonomous replication, the vector may further comprise an origin of replication enabling the vector to replicate autonomously in the host cell in question. The origin of replication may be any plasmid replicator that participates in the autonomous replication that functions in a cell. The expression "origin of replication" or "plasmid replicator" is defined herein as a nucleotide sequence that enables a plasmid or vector to replicate in vivo. Examples of origins of replication useful in a filamentous fungal cell are AMA1 and ANS1 (*Verdoes* et al., 2007, *Ind. Biotechnol.*, 3 (1)).

More than one copy of the nucleic acid sequence of the present invention can be inserted in the host cell to increase production of the gene product. An increase in the number of copies of the polynucleotide can be obtained by integrating at least one additional copy of the sequence in the genome of the host cell or by including a selectable, amplifiable marker gene with the polynucleotide, where the cells containing amplified copies of the selectable marker gene and, therefore, additional copies of the polynucleotide, can be selected by culturing the cells in the presence of the suitable selectable agent. The procedures used to ligate the previously described elements to construct the recombinant expression vectors referred to in the present invention are well known to the person skilled in the art.

In another aspect, the invention provides a host cell comprising the genetic construct of the invention, hereinafter called "host cell of the invention". Therefore, said host cell expresses the Cbh1 variant of the invention. The "host cell", as used herein, includes any cellular type which is susceptible to transformation, transfection, transduction and similar with the genetic construct of the invention. The host cell may be eukaryotic, such as a mammalian, insect, plant or fungal cell. In a preferred embodiment, the host cell is a filamentous fungal cell. The filamentous fungi are generally characterised by a mycelial wall composed of chitin, cellulose, glucan, chitosan, mannan and other complex polysaccharides. In a more preferred embodiment, the filamentous fungal host cell is an *Acremonium, Aspergillus, Aureobasidium, Bjerkandera, Ceriporiopsis, Coprinus, Coriolus, Cryptococcus, Filibasidium, Fusarium, Gibberella, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes* or *Trichoderma* cell.

In a more preferred embodiment, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another more preferred embodiment, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Gibberella zeae, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei* or *Trichoderma viride* cell. In another even more preferred embodiment, the host cell of the invention is any strain of the *Myceliophthora thermophila* species. In an even more preferred embodiment, the host cell of the invention is the C1 strain of the *Myceliophthora thermophila* species.

It shall be understood that, for the aforementioned species, the invention encompasses both perfect and imperfect states and other taxonomic equivalents, for example anamorphic, regardless of the species name by which they are known. The persons skilled in the art shall readily recognise the identity of appropriate equivalents. For example, *Myceliophthora thermophila* is equivalent to *Chrysosporium lucknowense*.

The term "expression" includes any stage involved in the production of the Cbh1 variant of the invention including, but not limited to, transcription, post-transcriptional modification, translation, post-translational modification and secretion.

The Cbh1 variant of the invention has greater cellobiohydrolase activity, so its use in an enzyme composition for the hydrolysis stage of cellulosic material into fermentable sugars in processes for the production of a bioproduct, preferably ethanol, is interesting to improve activity and performance of the entire enzyme composition.

Therefore, in another aspect of the invention an enzyme composition comprising the Cbh1 variant of the invention, hereinafter known as "enzyme composition of the invention", is provided. In a preferred embodiment, the enzyme composition of the invention further comprises other cellulolytic enzymes.

It shall be understood that the Cbh1 variant of the invention can be combined with one or more of the cellulolytic enzymes described herein or any other available and suitable enzyme to produce a multienzyme composition for cellulosic biomass saccharification. One or more components of the multienzyme composition (apart from the enzymes described in the present invention) can be obtained or derived from a microbial, plant or other type of source or combination thereof, and contain enzymes capable of degrading the cellulosic material.

This composition of the invention may further comprise other enzyme activities, such as aminopeptidase, amylase, carbohydrase, carboxypeptidase, catalase, cellulases such as endoglucanases, beta-glucosidases and/or cellobiohydrolases; chitinase, cutinase, cyclodextrin glucosyltransferase, deoxyribonuclease, esterase, alpha-galactosidase, beta-galactosidase, glucoamylase, alpha-glucosidase, haloperoxidase, invertase, laccase, lipase, mannosidase, oxidase, reductase, pectinolytic enzyme, peptidoglutaminasa, peroxidase, phytase, polyphenoloxidase, protease, ribonuclease, transglutaminase or xylanase, or any combination thereof. The additional enzyme(s) may be produced, for example, by means of a microorganism belonging to the genus *Aspergillus*, such as *Aspergillus aculeatus, Aspergillus awamori, Aspergillus fumigatus, Aspergillus foetidus, Aspergillus japonicus, Aspergillus nidulans, Aspergillus niger* or *Aspergillus oryzae; Fusarium*, such as *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium pseudograminearum, Fusarium reticulatum, Fusarium roseum, Fusarium sambucinum, Fusarium sarcochroum, Fusarium sulphureum, Fusarium toruloseum, Fusarium trichothecioides* or *Fusarium venenatum; Gibberella*, such as *Gibberella zeae; Humicola*, such as *Humicola insolens* or *Humicola lanuginosa; Trichoderma*, such as *Trichoderma harzianum, Trichoderma*

*koningii, Trichoderma longibrachiatum, Trichoderma reesei* or *Trichoderma viride*; *Penicillium*, such as *Penicillium brasilianum, Penicillium canescens, Penicillium chrysogenum, Penicillium decumbens, Penicillium ethinulatum, Penicillium funiculosum, Penicillium janthinellum, Penicillium pinophilum* or *Penicillium purpurogenum* or *Myceliophthora*, such as *Myceliophthora thermophila*.

The term "cellulolytic enzymes", also known as "cellulases", makes reference to a category of enzymes capable of hydrolyzing cellulose (β-1,4-glucan or β-D-glucosidic bonds) into shorter oligosaccharides such as for example, but not limited to, cellobiose and/or glucose. Examples of cellulolytic enzymes are, but not limited to, endoglucanases, beta-glucosidases, cellobiohydrolases, beta-xylosidases, alpha-xylosidases, xyloglucanases, polysaccharide monooxygenases, xylanases or arabinofuranosidases. Therefore, in a more preferred embodiment, these cellulolytic enzymes are selected from the list consisting of: endoglucanases, beta-glucosidases, cellobiohydrolases, beta-xylosidases, xyloglucanases, polysaccharide monooxygenases, xylanases, arabinofuranosidases or any combination thereof. These cellulolytic enzymes may be derived from the host cell of the invention or other cellulolytic enzyme-producing microorganisms other than the host cell of the invention. Likewise, they can be produced naturally or recombinantly and can be native or modified to present some advantageous property.

The term "endoglucanase" or "EG" makes reference to a group of cellulase enzymes classified as E.C. 3.2.1.4. These enzymes hydrolyze the β-1,4-glycosidic bonds of cellulose.

The term "beta-glucosidase" (E.C. 3.2.1.21), as used herein, refers to an enzyme that catalyzes the hydrolysis of a sugar dimer including, but not limited to, cellobiose, with the release of a corresponding sugar monomer, which is used, but not limited to, for ethanol synthesis. The beta-glucosidase enzyme acts on the β1→4 bonds that link two glucoses or molecules substituted for glucose (i.e. the cellobiose disaccharide). It is an exocellulase with specificity for a variety of beta-D-glucoside substrates. It catalyzes the hydrolysis of non-reducing terminal residue in beta-D-glucosides with glucose release.

The term "beta-xylosidase" (E.C. 3.2.1.37) refers to a protein that hydrolizes the short 1,4-β-D-xylooligomers into xylose.

The term "alpha-xylosidase" (E.C. 3.2.1.177) refers to the enzyme that facilitates the degradation of nonreducing xyloglucan residues to xylose and glucose.

The term "xylanase" or "endoxylanase" (EC 3.2.1.8) refers to the enzyme that catalyzes the endohydrolysis of 1,4-β-D-xylosidic bonds into xylanes.

The term "arabinofuranosidase" (EC 3.2.1.55) refers to the enzyme that catalyzes the hydrolysis of terminal nonreducing alpha-L-arabinofuranose residues into alpha-L-arabinosides.

The term "polysaccharide monooxygenase", "PMO", "Glycosyl-hydrolase of the 61 family" or "GH61" refers to an enzyme that breaks cellulose chains by oxidation of its glucose monomers in carbons 1,4 and/or 6 which, when included in a saccharification reaction (i.e. one in which endoglucanases, beta-glucosidases and cellobiohydrolases are used), results in a larger amount (higher yield) of one or more soluble sugars (for example, glucose) compared to the saccharification reaction carried out under the same conditions but in the absence of the GH61 protein or PMO. The PMO activity can be determined by, for example, oxidative indirect trials that colorimetrically demonstrate the phenomenon of electron transfer using different electron donors and acceptors compounds (Kitt et al., 2012, Biotechnology for Biofuels Vol. 5:79, pages 1-13). On the other hand, efficiency over biomass can be measured, for example, by combining the PMO polypeptide with cellulase enzymes in a saccharification reaction and determining whether there is an increase in glucose yield compared to the same saccharification reaction carried out in the absence of said polypeptide.

The term "xyloglucanase" (EC 3.2.1.151) refers to the enzyme that hydrolyzes the 1,4-beta-D-glucosidic bonds in the xyloglucan.

In a preferred embodiment, the enzyme composition of the invention further comprises the host cell of the invention.

The composition of the invention can be prepared according to procedures known in the art and may be in liquid form or be a dry composition. The enzymes to be included in the composition may be stabilised in accordance with procedures known in the art.

Another aspect described in the invention refers to the use of the host cell of the invention or the composition of the invention for the degradation of biomass.

The host cell or the composition of the present invention can be used to produce monosaccharides, disaccharides and polysaccharides from plant biomass as chemical or fermentation raw materials for the production of ethanol, plastics or other products or intermediates.

The host cell of the present invention can be used as a source of the Cbh1 variant of the invention and other polypeptides having cellulase activity, in processes for the saccharification or degradation or hydrolysis and fermentation of lignocellulosic material.

Therefore, in a preferred embodiment, the enzyme composition of the invention is an enzyme composition obtained (secreted) by the host cell of the invention. This composition can be obtained by culturing the host cell of the invention under conditions suitable for the production and secretion of cellulolytic enzymes.

The host cell can be cultured in a suitable nutrient medium, solid or liquid, to produce the Cbh1 variant of the invention and the whole enzyme composition of the invention, using procedures well known in the art. For example, the cell may be cultivated on small or large scale by means of culture shake flask fermentation (which includes continuous, discontinuous or batch fermentations, discontinuous or fed-batch or in solid state) carried out in a laboratory or industrial bioreactor in a suitable medium and under conditions that make it possible to express and/or isolate the variant or composition. The cultivation takes place in a suitable nutrient medium comprising carbon and nitrogen sources and inorganic salts, using procedures known in the art. If the variant is secreted along with other cellulolytic enzymes in the nutrient medium, they can be recovered directly from the medium.

The Cbh1 variant of the invention expressed together with other expressed cellulolytic enzymes can be detected using procedures known in the art specific to polypeptides. These detection procedures may include the use of specific antibodies, the formation of a product from enzyme or the disappearance of a substrate from enzyme.

The resultant Cbh1 variant of the invention, together with the other cellulolytic enzymes secreted by the host cell, can be recovered using procedures known in the art. For example, they can be recovered from the nutrient medium using conventional procedures including, but not limited to, centrifugation, filtration, extraction, spray drying, evaporation, or precipitation.

The Cbh1 variants produced in the present invention, together with other cellulolytic enzymes secreted by the host cell, can be purified by a variety of procedures known in the art including, but not limited to, chromatography (for example, ion exchange, affinity, hydrophobic, chromatofocusing and molecular size exclusion), electrophoretic procedures (for example, preparative isoelectric focusing), differential solubility (for example, precipitation in ammonium sulfate), SDS-PAGE, or extraction, in order to obtain the substantially pure enzymes that can be included in an enzyme composition.

The degradation or hydrolysis of cellulosic material into fermentable sugars, a process also known as "saccharification", by means of the Cbh1 variant of the invention, the host cell of the invention or the composition of the invention, may be accompanied afterwards by a fermentation process wherein the fermentable sugars obtained are used in order to finally obtain a bioproduct such as bioethanol.

Therefore, in another aspect, the present invention relates to a process for producing fermentable sugars from cellulosic biomass, hereinafter the "first procedure of the invention", which comprises:
 a) Incubating the cellulosic biomass with the Cbh1 variant of the invention, the host cell of the invention or the enzyme composition of the invention, and
 b) Recovering the fermentable sugars obtained after incubating in stage (a).

The term "fermentable sugar", as used herein, refers to simple sugars such as glucose, xylose, arabinose, galactose, mannose, rhamnose, sucrose or fructose.

In another aspect, the present invention relates to a process for producing a bioproduct from cellulosic biomass, hereinafter the "second procedure of the invention", which comprises:
 a) Incubating the cellulosic biomass with the Cbh1 variant of the invention, the host cell of the invention or the enzyme composition of the invention,
 b) Fermenting the fermentable sugars obtained after incubating in stage (a) with at least one fermenter microorganism, and
 c) Recovering the bioproduct obtained after fermenting in stage (b).

The expression "cellulosic biomass" means the biodegradable fraction of products, waste and residues of biological origin from agriculture (including vegetable, such as crop residues and animal substances), forestry (as timber resources) and related industries including fisheries and aquaculture as well as the biodegradable fraction of industrial and municipal waste, such as municipal solid waste or bins. In a preferred embodiment, the cellulosic material is straw or organic fraction of municipal solid waste. In a more preferred embodiment, the cellulosic material is plant biomass, more preferably selected from the list consisting of: biomass rich in fermentable sugars, such as sugarcane, starch biomass, for example, wheat grain or corn stover. Even more preferably, the plant biomass is cereal grain such as starch, wheat, barley or mixtures thereof.

In some embodiments, the first and/or second process of the invention preferably comprises a pretreatment process prior to stage (a). In general, a pretreatment process will give rise to components of the cellulosic biomass that are more accessible for subsequent stages or are more digestible by the enzymes after treatment in the absence of hydrolysis. Pretreatment uses various techniques including, but not limited to, chemical treatment (for example, ammonia fibre explosion or exposure to a solvent), physical treatment (for example, steam explosion at high temperatures), mechanical treatment (for example, grinding or milling), biological treatment or any combination thereof, to alter the structure of the cellulosic biomass and make the cellulose more accessible.

The term "recovery", as used herein, refers to the recovery of fermentable sugars obtained after incubation in stage (a) of the first procedure of the invention or of the bioproduct obtained after the fermentation of stage (b) of the second procedure of the invention. The recovery can be produced by any procedure known in the art, including mechanical or manual procedures.

The term "fermenter or fermentation", as used herein, refers to a biotransformation process produced by the activity of some microorganisms in which sugars such as glucose, fructose, and sucrose are converted into ethanol. The microorganisms used in this manner are fermenter microorganisms with fermentation capacity, such as yeasts of the genera *Saccharomyces, Pichia* or *Kluyveromyces*, preferably *Saccharomyces cerevisiae*, both natural hexose fermenting strains as genetically modified for the conversion of pentoses.

In another preferred embodiment, stages (a) and (b) of the second procedure of the invention can be carried out simultaneously.

The term "bioproduct" or "biological products" refers to the materials, chemicals and energy derivatives from renewable biological resources. Examples of these bioproducts are, but not limited to, hydrocarbon compounds in their different forms, such as aliphatic hydrocarbons (saturated, unsaturated, cyclic) or aromatic hydrocarbons, such as alkanes, alkenes, alkynes, cyclic forms of these compounds or aromatic hydrocarbons; oxygenated substances such as alcohols, ethers, aldehydes, ketones or carboxylic acids; nitrogenous substances such as amines, amides, nitrogen compounds or nitriles; halogenated substances such as halides. The term "bioproducts" also includes any combination of the compounds described above, compounds that derive from the compounds described above by means of any physical, chemical or biological treatment, polymers of the compounds described above, compounds described above substituted by any group or functional element in one or more of its links and branched forms of the compounds described above.

Ethanol can be produced by the enzymatic degradation of cellulosic material and the conversion of released saccharides to ethanol. This kind of ethanol is often called bioethanol. It can be used as a fuel additive or expander in blends of less than 1% and up to 100% (as a fuel substitute).

Therefore, in a more preferred embodiment, the bioproduct is biofuel. The term "biofuel" as used herein, makes reference to a hydrocarbon, or a mixture thereof, that can be used as fuel and is obtained by using fermentable cellulosic material as a starting material. Examples of biofuels include, but are not limited to, ethanol or bioethanol and biodiesel. In a preferred embodiment, the biofuel is bioethanol.

The term "bioethanol" or "ethanol" makes reference to an alcohol produced by means of fermentation, mainly from fermentable cellulosic material such as carbohydrates produced by means of the Cbh1 variant of the invention, or starch cultures such as corn or sugar cane.

Before (i.e. in stage (a)) and/or simultaneously with the fermentation of stage (b) of the second method of the invention, the biomass, preferably pretreated biomass, is hydrolyzed to degrade cellulose and hemicellulose to sugars and/or oligosaccharides. The solid content during hydrolysis may be, but not limited to, comprised between 10%-30% of total weight, preferably between 15%-25% of total weight, more preferably between 18%-22% of the total weight. The hydrolysis is performed as a process in which the biomass, preferably pretreated biomass, is incubated with the Cbh1 variant of the invention, the host cell of the invention or the composition of the invention and thus forms the hydrolysis solution. The appropriate process time, temperature and pH conditions can readily be determined by the person skilled in the art. Preferably, said hydrolysis is carried out at a temperature between 25° C. and 60° C., preferably between 40° C. and 60° C., and specifically at approximately 50° C. The process is preferably conducted at a pH in the interval of 4-6.5, preferably pH 4.5-5.5, and particularly approximately pH 5.2. Preferably, hydrolysis is performed in a time period comprised between 12 and 144 hours, preferably between 16 and 120 hours, more preferably between 24 and 96 hours, and even more preferably between 32 and 72 hours.

The hydrolysis (stage (a)) and fermentation (stage (b) of the second method of the invention) can be performed simultaneously (SSF process) or sequentially (SHF process). According to the invention, the hydrolyzed biomass, and preferably pretreated, is fermented by at least one fermenter microorganism capable of fermenting fermentable sugars such as glucose, xylose, mannose and galactose directly or indirectly into the desired fermentation product. Fermentation is preferably carried out in a time between 8 and 96 hours, preferably between 12 and 72, and more preferably between 24 and 48 hours. In another preferred embodiment, fermentation is performed at a temperature between 20° C. and 40° C., preferably from 26° C. to 34° C., and particularly at approximately 32° C. In another preferred embodiment, pH is between 3 and 6 units, and preferably between 4 and 5. A yeast of the species *Saccharomyces cerevisiae* is preferred for ethanolic fermentation, preferably strains which are resistant to high levels of ethanol of up to, for example, 5% or 7% vol. of ethanol or more, such as 10%-15% vol. of ethanol.

Unless otherwise defined, all the technical and scientific terms used herein have the same meaning that they would be given by the person skilled in the art to which this invention belongs. In the practice of the present invention, procedures and materials similar or equivalent to those described herein may be used. Throughout the description and claims, the word "comprises" and its variations are not intended to exclude other technical characteristics, additives, components or stages. Other additional objects, advantages and characteristics of the invention will become apparent to those skilled in the art from the analysis of the description or may be learned by the practice of the invention. The following examples and drawings and sequence listing are provided by way of illustration and are not intended to be limiting of the present invention.

EXAMPLES

Example 1. Deletion of Gene cbh1 in *Myceliophthora thermophila* C1

To build a Δcbh1 strain in *M. thermophila* C1, the first step was the construction of a plasmid for deleting the cbh1 gene (SEQ ID NO: 1). Said plasmid contains upstream and downstream fragments of the cbh1 gene so that through homologous recombination with the genome of *M. thermophila* C1, the cbh1 gene was replaced by the selectable marker cloned between the two fragments. The upstream fragment of the cbh1 gene was amplified from the genomic DNA of *M. thermophila* C1 (obtained using the DNeasy Plant Mini Kit from Qiagen) with DNA polymerase iProof High-Fidelity (BioRad) using oligonucleotides 1 and 2 (SEQ ID NO: 10 and 11, respectively).

```
Oligonucleotide 1:
                                            (SEQ ID NO: 10)
CCGCGGTGGCGGCCGCTCTAGACGCTGCACTGTGGCACGACTACCAGTG
ATC Oligonucleotide 2:
                                            (SEQ ID NO: 11)
GCTGCAGCCCGGGGGATCCCCAGGCTAATTGTCGCGTCGCTTCGGACGG
ACA
```

These oligos include the recognition sequences for restriction enzymes XbaI and BamHI. Likewise, the downstream fragment of the cbh1 gene was amplified with oligonucleotides 3 and 4 (SEQ ID NO: 12 y 13 respectively).

```
Oligonucleotide 3:
                                            (SEQ ID NO: 12)
CATGGTCATAGAATTCGATATCAACCTCTCTGAAGGAGGTTCTGAGACA
CGC Oligonucleotide 4:
                                            (SEQ ID NO: 13)
TGGGTACCGGGCCCCCCCTCGAGCTAGAAGAAGGGCGTAAATAAGAAGC
TATAATAGCTT
```

Figure 1:
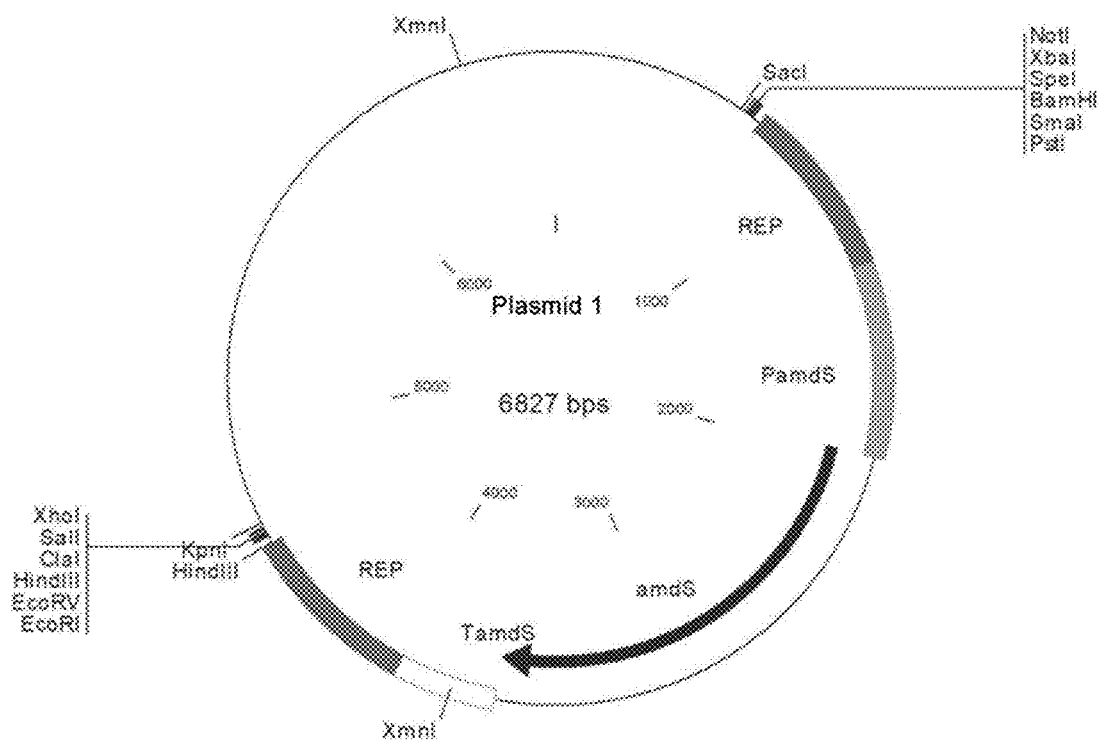
FIG. 1. Schematic representation of plasmid 1, which makes it possible to clone the flanking ends of the gene intended to be deleted. It includes the amdS gene as a selection marker that confers resistance to acetamide. The selection marker includes its promoter (PamdS) and terminator (TamdS) region. On both sides of the amdS gene are two REP (repeated) regions which enable the deletion of the amdS selection marker once the vector has been integrated in the genome by homologous recombination therebetween.

These oligonucleotides include the recognition sequences for restriction enzymes EcoRV and XhoI. The amplification conditions for both fragments were a cycle at 98° C. for 30 seconds and 35 cycles at 98° C. for 10 seconds, 64° C. for 30 seconds, 72° C. for 45 seconds and 72° C. for 10 minutes. Upon amplifying the upstream and downstream fragments of the cbh1 gene, with fragment sizes corresponding to 1400 bp each, they were cloned into the plasmid vector 1 (FIG. 1).

Figure 2:
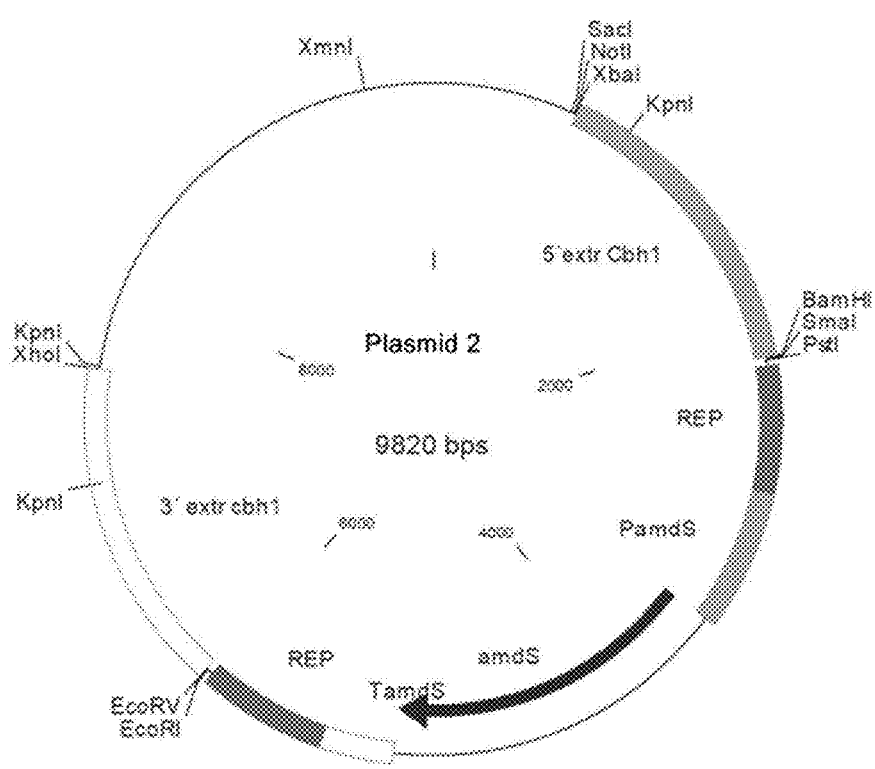
FIG. 2. Schematic representation of plasmid 2 used to delete the cbh1 gene. The upstream region (region 5') and downstream region (region 3') of the cbh1 gene have been cloned into plasmid 1.

This vector contains the amdS gene as a selection marker, which confers the ability to use acetamide as a nitrogen source. First, the amplified fragment corresponding to the 3' end of the gene (located downstream thereof) was digested with the restriction enzymes EcoRV-XhoI and was cloned into the plasmid vector 1 previously digested with the same restriction enzymes. The ligation mixture was transformed into electrocompetent *Escherichia coli* XLI Blue MRF cells following the protocol provided by the manufacturer (Stratagene). Upon obtaining this plasmid, cloning of the upstream end of the cbh1 gene continued. To this end, the corresponding fragment was digested with the restriction enzymes XbaI-BamHI and was cloned into the plasmid where the downstream end had been previously cloned. The ligation mixture was transformed into electrocompetent *Escherichia coli* XLI Blue MRF cells following the protocol provided by the manufacturer (Stratagene). The plasmid obtained (plasmid 2) is shown in FIG. 2.

The plasmidic DNA for deleting the cbh1 gene was linearised by means of digestion with the restriction enzymes SacI and XhoI and was used to transform cells of the *M. thermophila* C1 strain (Verdoes et al., 2007, *Ind. Biotechnol.*, 3 (1)). This DNA was introduced into the host strain using a protoplast transformation method (U.S. Pat. No. 7,399,627B2). The transformants were sown on agar plates containing 0.6 g/l of acetamide (Merck). After 5 days of incubation at 35° C., a hundred transformants that expressed the amdS gene were analysed and, therefore, were capable of growing in the presence of acetamide as sole source of nitrogen. The transformants obtained were genetically analysed to verify whether the cbh1 gene was substituted by the selection marker. To this end, genomic DNA was obtained from the transformants (obtained using the DNeasy Plant Mini20 Kit from Qiagen) and different PCR verifications were performed. The first PCR was performed by the DNA polymerase iProof High-Fidelity (BioRad) using oligonucleotides 5 and 6 (SEQ ID NO: 14 and 15, respectively) to amplify an internal fragment of cbh1 of 360 pb.

```
Oligonucleotide 5
                                            (SEQ ID NO: 14)
AACAAGTGGGATACTTCGTACT Oligonucleotide 6
                                            (SEQ ID NO: 15)
ATCCATGGACACGAAGTAGAG
```

Figure 3:
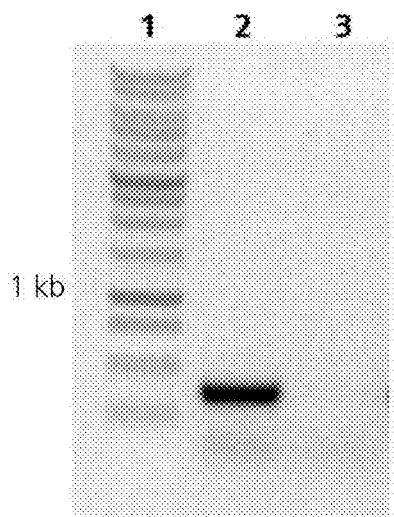
FIG. 3. Genetic verification of the deletion of the cbh1 gene. PCR amplification of an internal fragment of 360 pb of the cbh1 gene. Lane 1: Marker, Lane 2: Parental strain, Lane 3: Δcbh1 Strain.

The amplification conditions were a cycle at 95° C. for 4 minutes and 30 cycles at 95° C. for 30 seconds, 55° C. for 30 seconds, 72° C. for 30 seconds and 72° C. for 10 minutes. In this example, the host cells which have been transformed and do not express the cbh1 gene (negative amplification) with respect to the host cells that express the gene (positive amplification) are identified. These amplification results are shown in FIG. 3.

Example 2. Evaluation of the *M. thermophila* C1 Δcbh1 Strain

Production of Enzyme Cocktails

Figure 4:
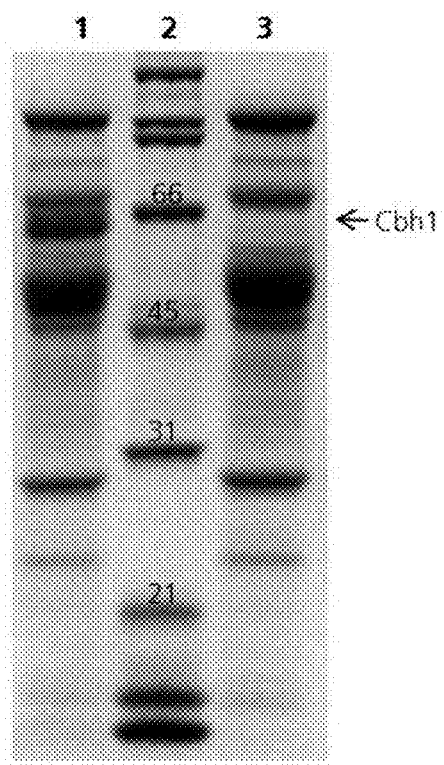
FIG. 4. Electrophoresis in polyacrylamide gel (SDS-PAGE 12%) of the enzyme cocktail of a parental strain and of the strain lacking the cellobiohydrolase enzyme. Lane 1: enzyme composition of the parental strain, Lane 2: molecular weight marker and Lane 3: enzyme composition of the Δcbh1 strain. The arrow indicates the height at which the protein band corresponding to the Cbh1 enzyme migrates.

The production of enzyme cocktails of the parental strain and the Δcbh1 strain was performed following the methodology described by Verdoes et al. 2007 and Visser et al., 2011, Ind. Biotechnol. (3). Two different enzyme cocktails were produced; a control cocktail and a Δcbh1 cocktail. The control cocktail consisted of the mixture of extracellular enzymes produced by the unmodified *M. thermophila* C1 strain in the production conditions described in the previously provided references. FIG. 4 shows the electrophoresis in acrylamide gel in denaturing conditions (SDS-PAGE) of the enzyme compositions with and without Cbh1, wherein the absence of a band of approximately 66 KDa corresponding to the glycosylated Cbh1 enzyme can be observed.

Figure 5:
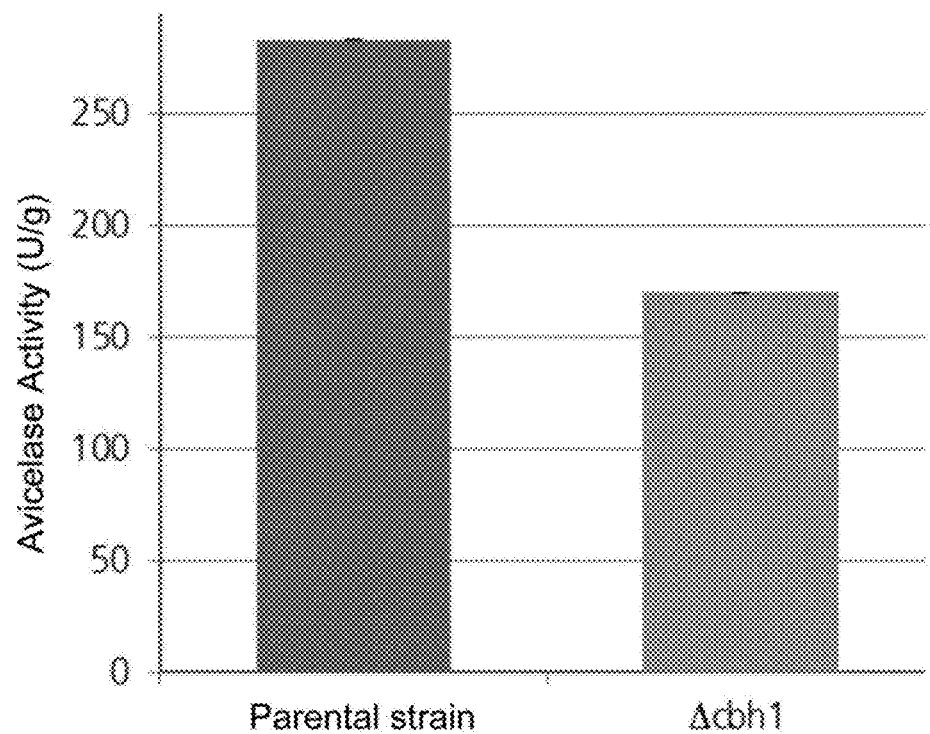
FIG. 5. Measurement of avicelase activity of the Cbh1 enzyme. Assay on avicelase activity of the enzyme cocktails of the parental strain of *M. thermophila* and another lacking said enzyme (Δcbh1 strain). All the measurements were analysed in triplicate and the error bars correspond to the standard deviation.

Measurement of the Cellobiohydrolase Activity of an Enzyme Cocktail Produced by *M. thermophila* C1 Δcbh1 and its Parental Strain Cellobiohydrolases (EC 3.2.1.9.1) catalyse the breakage of a cellobiose molecule into two glucose molecules. The cellobiohydrolase activity of the parental and Δcbh1 cocktails was measured using the Avicel substrate (microcrystalline cellulose). For this avicelase assay, the enzyme reaction mixtures (1 ml final volume) contain 200 µL of sodium acetate buffer (pH 5.0, 200 mM), 10 mg of Avicel and 50 µg of the enzyme cocktail. 100 µg of the β-glucosidase enzyme were added to this mixture for the production of glucose from the cellobiose generated by the activity of the cellobiohydrolases present in both enzyme cocktails. This mixture was incubated at 50° C. for 120 minutes at 1400 rpm agitation. The reaction was stopped by incubating the mixture for 10 minutes at 99° C. The samples were subsequently centrifuged for 5 minutes at 4000×g. For the correct measurement of the concentration of glucose produced in the enzyme reaction, the GOPOD enzyme method (Glucose oxidase/peroxidase) (Enzymatic method for glucose determination using the GOPOD Kit from Megazyme) was used according to manufacturer's specifications (FIG. 5). A unit of activity of Avicel hydrolysis was defined as the amount of enzyme equivalent to the release of 1 µmol of cellobiose per minute. The protein concentration of the parental and Δcbh1 cocktails was quantified using the BCA AppliChem Kit (Ref. A7787), after having treated the sample with the "Compat-Able Protein Assay Preparation Reagent Set (Thermo Scientific Ref. 23215)" kit, both according to the manufacturer's specifications. As can be observed in FIG. 5, the Δcbh1 strain shows less avicelase activity than the parental strain; its activity is due to other cellobiohydrolases present in the cocktail.

Evaluation of the *M. thermophila* Host Strains Which Lack Cbh1 Cellulase with Respect to the Parental Strains that Contain It The release of fermentable sugars in the *M. thermophila* C1 Δcbh1 strain was compared with its parental strain. Pretreated corn biomass (pretreated corn stover o PCS) was used as substrate for enzyme hydrolysis. The pretreatment was performed by means of a steam explosion system (Nguyen et al., 1998, Appl. Biochem. Biotechnol. 70-72) and its compositional analysis was performed in accordance with the procedures described by NREL in "Standard Biomass Analytical Procedures". With the object of using it in the hydrolysis, the biomass was previously neutralised and adjusted to a pH of 5.5. For the enzymatic hydrolysis process, 100 ml ISO flasks were used with 20 g of the reaction mixture at 20% (w/w) of total solids and supplemented with 12 mg of protein per gram of glucan of the cocktail from the parental and Δcbh1 strains, respectively. The flasks containing the mixture were incubated for 72 hours at 50° C. with 150 rpm agitation in a 25 mm diameter orbital incubator (Infors HT). Upon completing the process, the glucose content of the samples resulting from the hydrolysate (slurry) was analysed by HPLC (Agilent Technologies, 1200 Series) using a refraction index detector (RID) and an Aminex column HPX-87 H).

Figure 6:
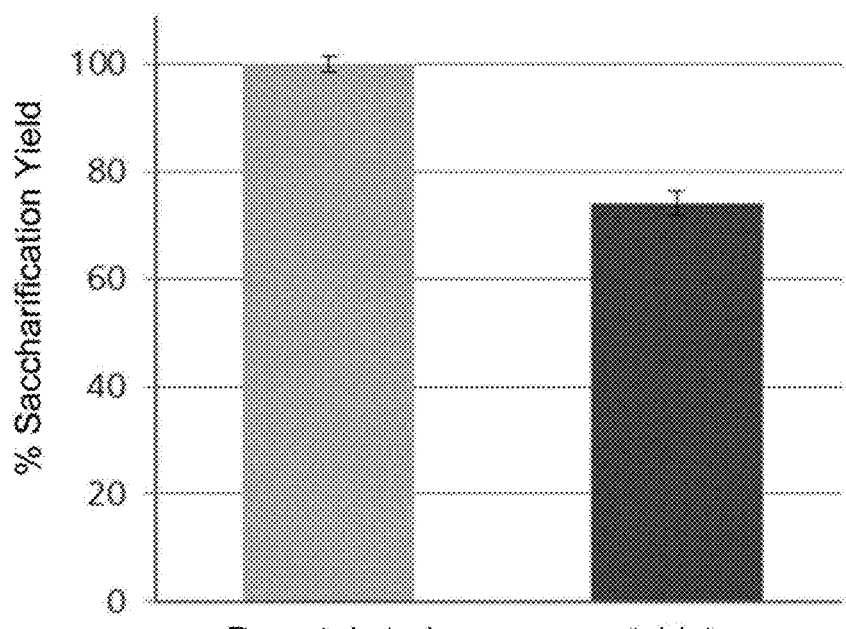
FIG. 6. Assay on hydrolysis of lignocellulosic biomass (corn stover). Analysis of glucose release from biomass subjected to a cellulolytic enzyme composition derived from a strain of *M. thermophila* that does not express the cbh1 gene (Δcbh1), with respect to the parental strain of *M. thermophila*. All the measurements were analysed in duplicate and the error bars correspond to the standard deviation.

The results obtained are shown in FIG. 6, where it can be observed that the deletion of the Cbh1 causes a drop in saccharification capacity of approximately 20% with respect to the control that expressed Cbh1.

Example 3. Mutagenesis of cbh1. Construction of an Expression Vector, Mutagenesis, Amplification of the Banks with Wutations in cbh1

The cbh1 gene was amplified from genomic DNA with oligonucleotides 7 and 8 (SEQ ID NO: 16 and 17, respectively), which include the sequences of the restriction enzymes NdeI and EcoRI at the ends (NdeI at the 5' end and EcoRI at the 3' end) to subsequently be cloned into the expression vector plasmid 3.

```
Oligonucleotide 7: (SEQ ID NO: 16):
CCGACATATGAAGCAGTACCTCCAGTACCTCGC

Oligonucleotide 8: (SEQ ID NO: 17):
GCTGAATTCTTAGACGTTGACAGTCGAGCCGATGG
```

Figure 7:
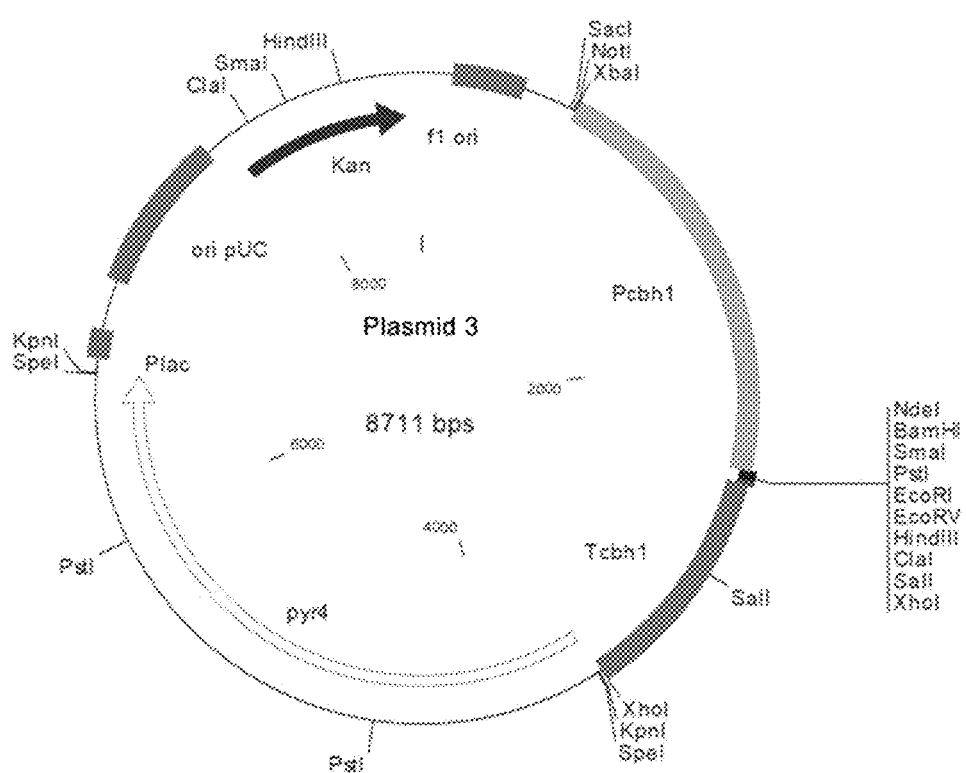
FIG. 7. Schematic representation of plasmid 3 used to express the cbh1 gene in *M. thermophila*. This plasmid contains the promoter and terminator of the cbh1 gene, Pcbh1 and Tcbh1, respectively. And it also contains the pyr4 marker for selection thereof.

This expression vector contains upstream the cbh1 promoter sequence (Pcbh1, 1796 pb) and downstream the terminator sequence of the same gene (Tcbh1, 1009 pb), in addition to the pyr4 gene (access number in the NCBI XP_003666633.1) of the same strain as selection marker. The pyr4 gene encodes a functional orotidine-5"-phosphate-decarboxylase and its expression vector makes it possible to supplement uridine auxotrophy in the corresponding auxotrophic *M. thermophila* C1 host strain (pyr4). The expression vector (plasmid 3) is shown in FIG. 7.

Figure 8:
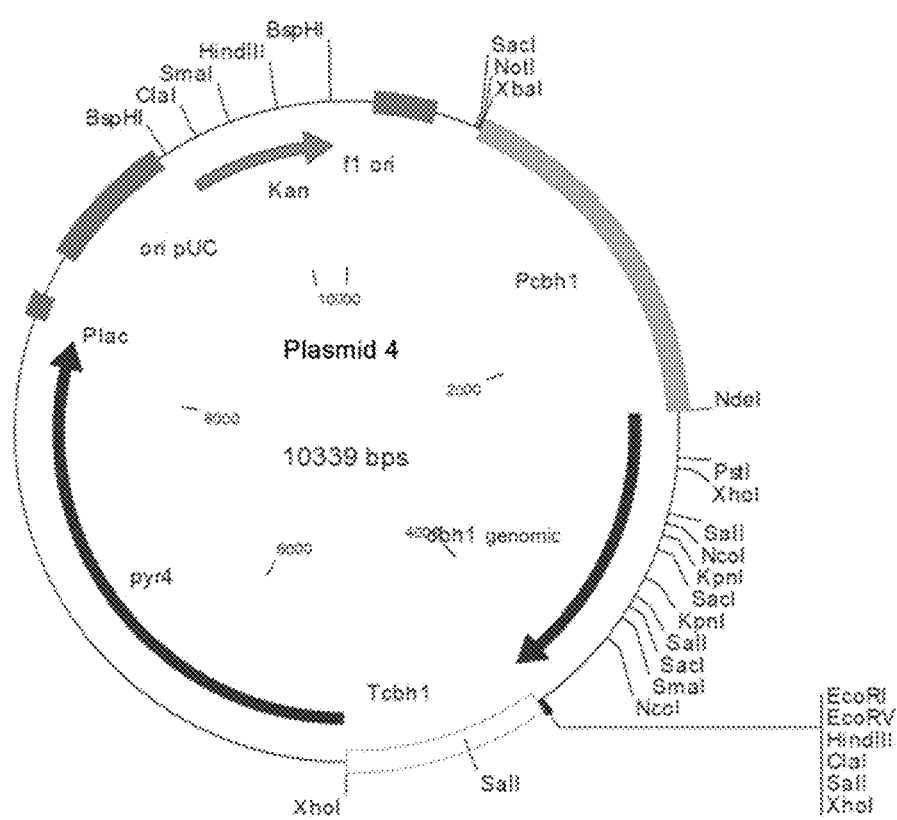
FIG. 8. Schematic representation of plasmid 4 used as a basis for the cbh1 mutant bank. The cbh1 gene was cloned into plasmid 3 downstream from its own promoter (Pcbh1).

The fragment containing the cbh1 gene was digested with the restriction enzymes NdeI and EcoRI and cloned into plasmid 3, previously digested with the same restriction enzymes. The expression vector and the gene were ligated and the product of the union was transformed into electrocompetent *Escherichia coli* XL1Blue MRF cells. The final plasmid is shown in FIG. 8.

The cbh1 gene cloned into plasmid 3 was subjected to random mutagenesis by means of PCR amplification using the GeneMorph II EZClone Domain Mutagenesis Kit (Agilent Technologies Inc.). Mutagenic amplification was performed using oligonucleotides 9 and 10 (SEQ ID NO: 18 and 19 respectively).

```
Oligonucleotide 9 (SEQ ID NO: 18):
GTGCTGATCCTCTTCCGTCCCATATG

Oligonucleotide 10 (SEQ       ID NO: 19):
CTCGAGGTCGACGGTATCGATAAG
```

The GeneMorph II EZClone Domain Mutagenesis system allows different mutation rates depending on the amount of target DNA and the amplification cycles used during the process. With these premises, a mutant bank was generated at a mutation frequency between 1 and 4.5 mutations/kb. The amount of initial template DNA was 0.5 µg of plasmid 4. The conditions for the amplification reaction were a cycle at 95° C. for 1 minute, followed by 25 cycles at 95° C. for 30 seconds, 60° C. for 30 seconds and 72° C. for 1.45 minutes. The thermocyclator was maintained at 72° C. for 10 minutes, followed by a cycle at 12° C. The PCR products corresponding to mutated versions of cbh1 were purified in agarose gel using an QlAquick gel extraction kit (Qiagen) and were used as megaprimers in a second PCR to amplify plasmid 4 in its entirety in the following conditions: a cycle at 95° C. for 1 minute and 25 cycles at 95° C. for 50 seconds, 60° C. for 50 seconds and 68° C. for 24 minutes. The amplification reactions were digested with DpnI (10 U/µl) for 2 hours at 37° C. to remove the parental expression plasmid used as a target, since DpnI only recognises methylated DNA. Therefore, only the plasmids amplified during this second PCR reaction remain after digestion with DpnI.

Both mutation banks were transformed into ultracompetent *Escherichia coli* XL-10 Gold cells following the protocol provided by the manufacturer (Agilent Technologies Inc.) and the plasmidic DNA was removed using the Plasmid Maxi Kit (Omega Bio-Tek, Inc.) from a total of 7,000 colonies transformed using both mutant banks.

Example 4. Transformation of the cbh1 Mutant Banks into *Myceliophthora thermophila* C1 and Selection of an Improved Version of cbh1

The plasmidic DNA of the cbh1 mutant banks was introduced in the *M. thermophila* pyr4 host strain using a protoplast transformation method (U.S. Pat. No. 7,399,627B2). The transformants were sown on agar plates without uridine supplement. After 5 days of incubation at 35° C., the resulting prototrophic transformants were analysed by means of saccharification assays in high yield or high throughput screening format (U.S. Pat. No. 7,794,962B2) using 96-well plates.

Figure 9:
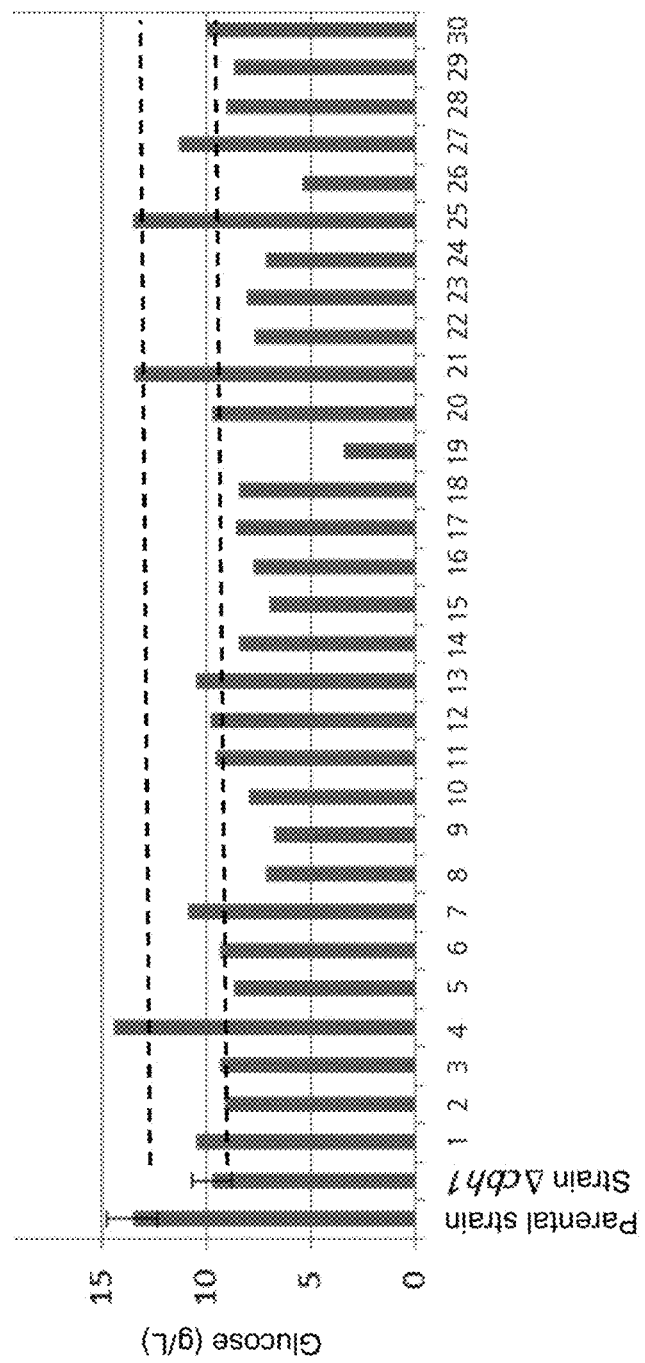
FIG. 9. Sample screening results in a microtiter plate. In each screening plate, each of the transformants is represented against the amount of glucose released in units g/l. The parental strain of *M. thermophila* that expresses the cbh1 gene and the deleted strain of this gene (Δcbh1) were used as a control. All the measurements were analysed in duplicate and the error bars correspond to the standard deviation.

The objective of the selection or screening was to identify the mutated versions of cbh1 with high glucose release. FIG. 9 shows an example of the results of glucose release on a microtiter plate obtained during the selection. All the transformants that released an average amount of glucose greater than double the standard deviation, with respect to that produced by the control, were confirmed in a second assay on microtiter plates.

Some of the positive transformants were confirmed by scale fermentation flask, and the production of the enzyme cocktails of interest and its evaluation by pretreated biomass saccharification were performed as previously indicated.

Figure 10:
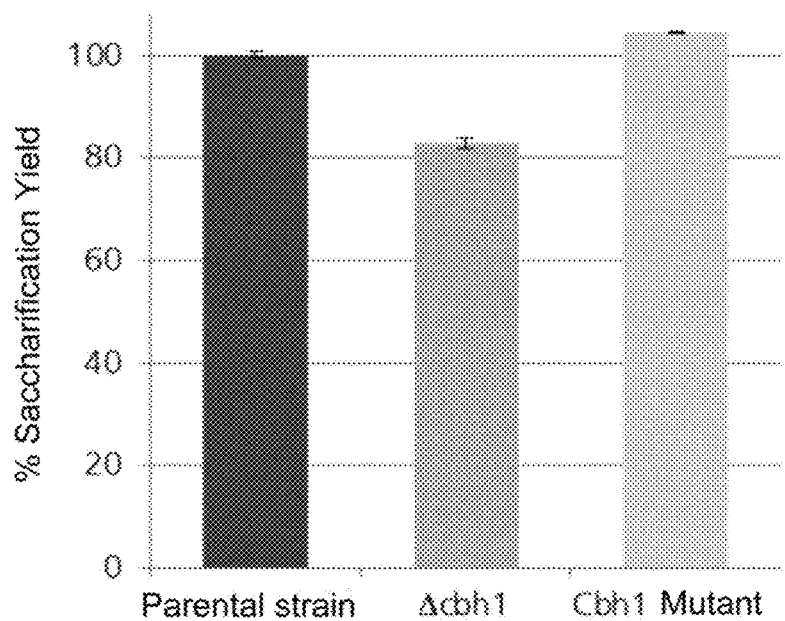
FIG. 10. Hydrolysis assay on lignocellulosic biomass (corn stover) of the *M. thermophila* strain with the Cbh1 mutant enzyme. Analysis of glucose release from biomass subjected to a cellulolytic enzyme composition derived from a strain of *M. thermophila* that expresses the mutant Cbh1 gene (Cbh1 Mutant), with respect to the parental strain of *M. thermophila* and to the strain that does not express it (Δcbh1). All the measurements were analysed in duplicate and the error bars correspond to the standard deviation.
Figure 11:
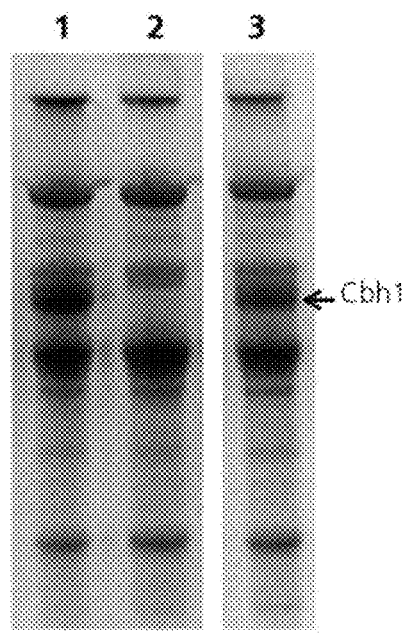
FIG. 11. Electrophoresis in polyacrylamide gel (SDS-PAGE 12%) of the enzyme cocktail of the parental strain (Lane 1), of the Δcbh1 strain (Lane 2) and the strain containing the mutated enzyme (Lane 3).

FIG. 10 shows the results of glucose release from biomass subjected to the enzyme composition derived from the *M. thermophila* cell that expresses the mutant Cbh1 gene with respect to the parental strain and to the strain that does not express the enzyme (Δcbh1), where a higher saccharification yield of the mixture containing the mutant Cbh1 can be observed. Electrophoresis in denaturing conditions (SDS-PAGE) of the cocktails produced by the parental strain, the strain which does not express the enzyme and the strain expressing the mutant Cbh1 can be observed in FIG. 11.

In order to determine the sequence of the expressed cbh1 gene, the DNA fragment corresponding to the mutant cbh1 gene was amplified from genomic DNA using oligonucleotides 9 and 10 (SEQ ID NO: 18 y 19 respectively).

Oligonucleotides 9 and 10 were used to amplify the Pcbh1-cbh1 cassette using genomic DNA of the transformants selected for their greater saccharification activity (obtained using the DNeasy Plant Mini Kit from Qiagen) with the DNA polymerase iProof High-Fidelity (BioRad).

The amplification was performed by means of a cycle at 98° C. for 2 minutes and 35 cycles at 98° C. for 10 seconds, 60° C. for 30 seconds and 72° C. for 2.15 minutes. The thermocyclator was maintained at 72° C. for 10 minutes, followed by a maintenance cycle at 12° C. The amplified DNA fragment was digested with the restriction enzymes NdeI and EcoRI and cloned into plasmid 3, previously digested with the same restriction enzymes. The ligation mixture was transformed into electrocompetent *Escherichia coli* XLI Blue MRF cells following the protocol provided by the manufacturer (Stratagene).

Figure 12:
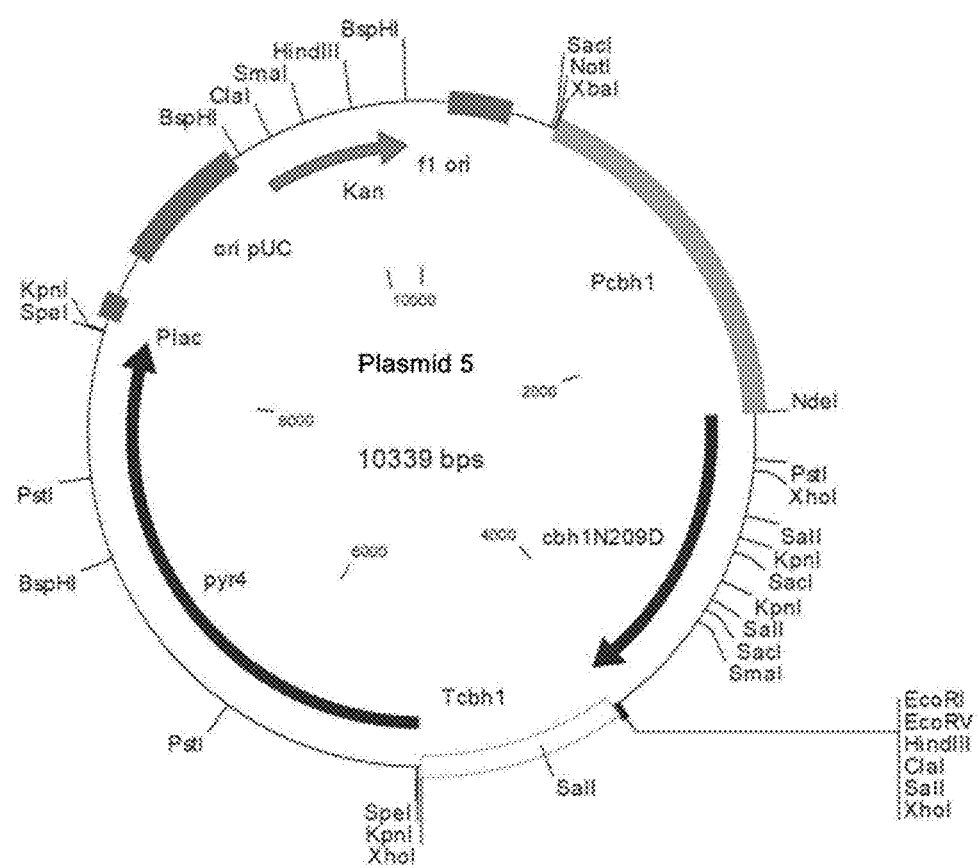
FIG. 12. Schematic representation of plasmid 5. Plasmid containing the cbh1 gene mutated in residue 209.

Both chains of the mutated versions of the cbh1 gene were sequenced using the Sanger Method. The mutated gene showed the point mutation implied by exchanging an adenine (in position +692) of the nucleotide sequence of native cbh1 SEQ ID NO: 1, by a guanine, giving rise to the nucleotide sequence SEQ ID NO: 4. This sequence encodes for a protein SEQ ID NO: 5 wherein the asparagine (N) in residue 209 of the native protein of SEQ ID NO: 2 had been exchanged by aspartic acid (D). Plasmid 5 (FIG. 12) was transformed into *M. thermophila* C1 to confirm the phenotype of improved glucose release.

Example 5. Comparative Analysis Between the Purified Protein Cbh1N209D and the Native Cbh1 Protein Purification of the Native Cbh1 and Mutant Cbh1 N209D Enzymes Both the mature native Cbh1 enzyme (SEQ ID NO: 3) and the mature Cbh1N209D protein (SEQ ID NO: 6) were purified using an ion exchange chromatography. The samples were prepared centrifuging the extracellular broths at 21,000×g for 45 minutes. The sediments were discarded and the supernatants were filtered through a 0.45 µm nylon filter (VWR). The resulting enzyme preparations diluted 1:2 in deionised $H_2O$ type 1 (5 g samples) were introduced in a HiLoad 26/10 Q-Sepharose HP column (GE Healthcare) balanced with the Tris-HCl 50 mM buffer at pH 7.0. The column was washed with the starting buffer and the linked proteins eluted with a gradient of NaCl at a flow rate of 5 ml $min^{-1}$ using a linear elution profile of 0% to 30%. The different samples obtained during the elution were analysed in denaturing polyacrylamide gels. Those fractions enriched in the expected band of 66 KDa that showed avicelase activity were selected. Ammonium sulfate at 30% was added to the previously chosen fractions and they were introduced in a HiLoad 26/10 Phenyl-Sepharose HP (GE Healthcare) hydrophobic interaction column, previously balanced with 100 mM sodium phosphate buffer, 1 M ammonium sulfate, at pH 7.0. The column was washed with the starting buffer and the linked proteins eluted with a descending gradient of ammonium sulfate at a flow rate of 5 ml $min^{-1}$ using a linear elution profile of 0 to 100%. Samples of parental Cbh1 and mutant Cbh1 N209D proteins were obtained with a purity degree of >95%.

Figure 13:
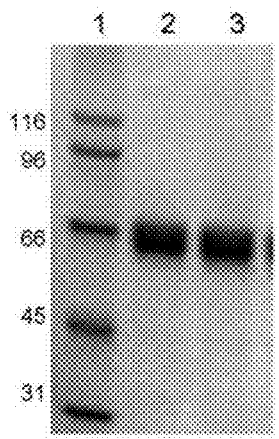
FIG. 13. Electrophoresis in polyacrylamide gel (SDS-PAGE 7.5%) showing the purified native Cbh1 and mutant Cbh1N209D enzymes. Lane 1: Molecular weight marker; Lane 2: Cbh1 native enzyme; Lane 3: Cbh1N209D mutant enzyme.

As shown in FIG. 13, after an electrophoresis in denaturing conditions (SDS-PAGE) both the parental Cbh1 and mutant Cbh1N209D protein show the same molecular mass.

Characterisation of Optimum pH of the Cbh1 N209D Enzyme

The avicelase assay was used to determine the optimum pH of the Cbh1N209D protein against the native Cbh1 protein, varying the buffer to change the pH of the reaction. In this case, similar buffers were used to study the activity of said enzymes in a pH range of 4-7. Avicelase activity values were represented as relative percentage compared to the greater activity obtained in each case.

Figure 14:
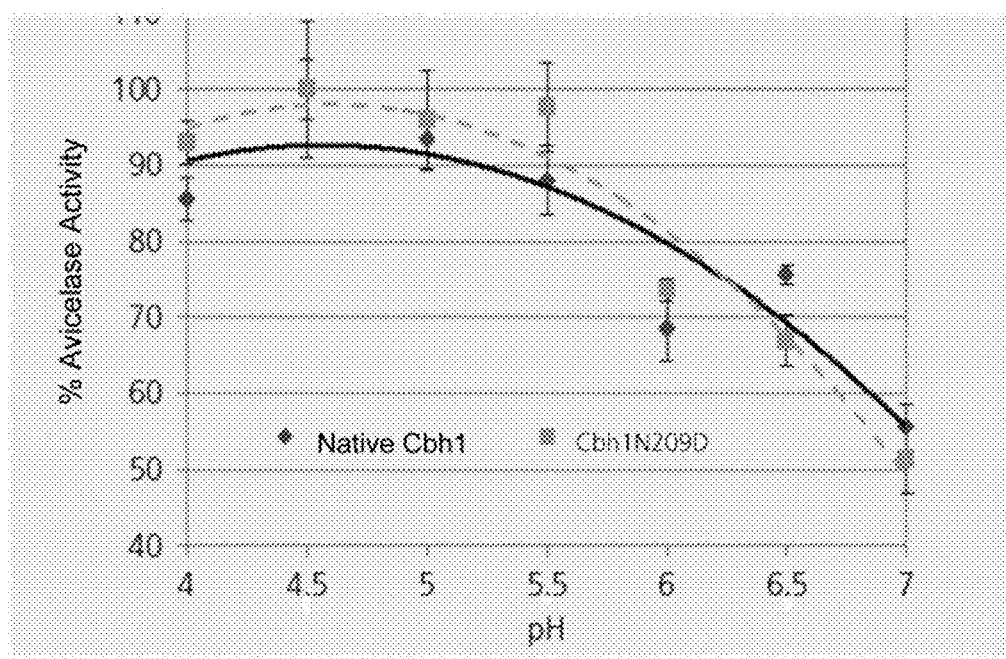
FIG. 14. Optimum pH study of the mature Cbh1N209D protein against native Cbh1 protein. The buffers used for each pH were: pH 4-6 Sodium acetate 200 mM and pH 6.5-7 Sodium phosphate 200 mM. All the measurements were analysed in duplicate and the error bars correspond to the standard deviation.

As shown in FIG. 14, both proteins showed a similar optimum pH range in the presence of avicel and maximum activity at pH 4.5-5.

Characterisation of the Stability of the Cbh1N209D Enzyme During the Biomass Saccharification Process The stability of the purified Cbh1 and Cbh1N209D enzymes was analysed in hydrolysis process conditions by means of the avicel assay. To determine stability throughout this process, purified enzymes were diluted at the same concentration in sodium acetate buffer 200 mM at pH 5 and incubated with 150 rpm agitation in a 25 mm diameter orbital incubator (Infors HT) for 72 hours at 50° C., taking samples at 0, 24, 48 and 72 hours.

Figure 15:
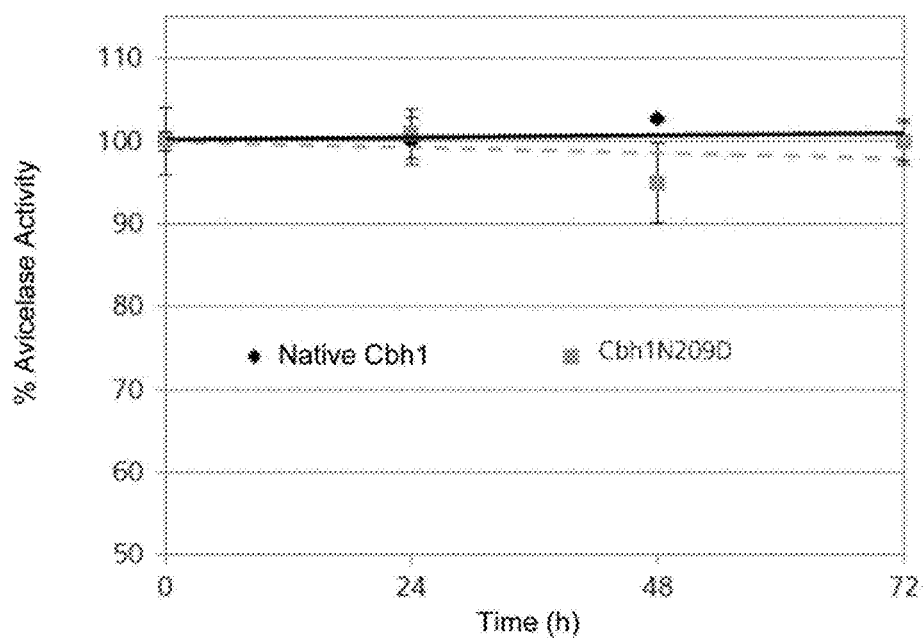
FIG. 15. Stability study of the Cbh1N209D mature protein against the native Cbh1 protein. Avicelase activity of the native Cbh1 and Cbh1N209D samples in the hydrolysis process conditions expressed in percentages. All the measurements were analysed in duplicate and the error bars correspond to the standard deviation.
Figure 16:
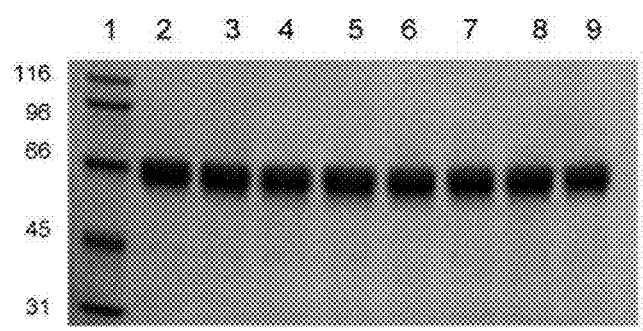
FIG. 16. Stability study of the mature protein Cbh1N209D against the native protein Cbh1 visualised in denaturing SDS-PAGE 7.5% polyacrylamide (Lane 1: Molecular weight marker; Lanes 2, 3, 4 and 5: Unincubated native Cbh1 protein, and incubated for 24, 48 or 72 hours, respectively; Lanes 6, 7, 8 and 9: Unincubated mutant protein Cbh1 N209D, and incubated for 24, 48 or 72 hours, respectively).

Assays on avicelase were subsequently performed and activity was represented as a relative percentage compared to the activity of the initial sample. Samples of different process times were also analysed by means of denaturing SDS-PAGE gel. As shown in FIG. 15, both proteins retained 100% of their activity throughout the described process, which coincides with the pattern observed in the polyacrylamide gel (FIG. 16), in which it is confirmed that neither of the two proteins apparently suffers any variation.

Example 6. Evaluation of the Mutant Cbh1N209D Enzyme in Comparison to the Wild-Type Cbh1 Enzyme of *M. thermophila* C1

The release of fermentable sugars of the *M. thermophila* C1 Δcbh1 strain supplemented with the mutant Cbh1N209D enzyme was compared with the same strain supplemented with the parental Cbh1 protein. As mentioned earlier, pretreated corn biomass (pretreated corn stover or PCS) was used as a substrate for enzyme hydrolysis and the hydrolysis process was performed using a reaction mixture at 20% (w/w) of total solids and supplemented with 12 mg of protein/g glucan in the case of the cocktails from the parental and Δcbh1 strains, and with 9.6 mg/g glucan plus 2.4 mg/g glucan of the corresponding purified protein in each case. The tubes containing the mixture were incubated for 72 hours at 50° C. with 150 rpm agitation in a 25 mm diameter orbital incubator (Infors HT). At the end of the process, the glucose content in the resulting hydrolysate (slurry) samples was analysed by means of HPLC, as indicated previously.

Figure 17:
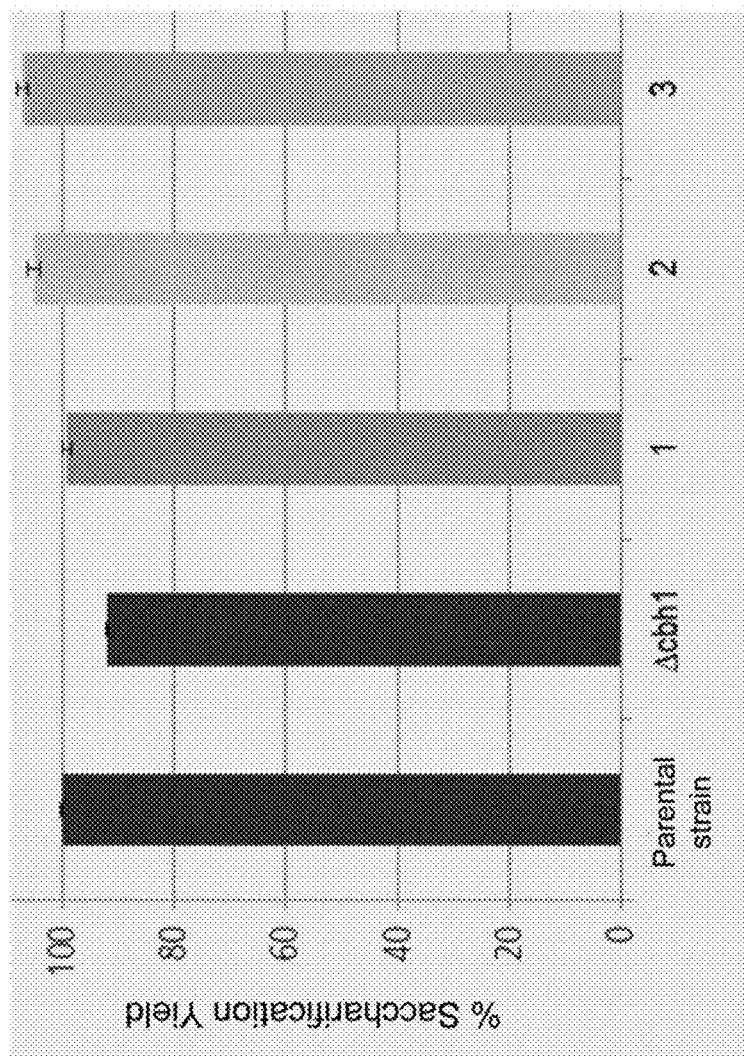
FIG. 17. Release of glucose by cocktails produced by *M. thermophila* Δcbh1 supplemented with native Cbh1 protein or with Cbh1 protein mutated in N209 residue. From left to right, it is shown the release of glucose by a parental strain of *M. thermophila*, strain of *M. thermophila* Δcbh1, the previous strain supplemented with (1) the purified Cbh1 of a parental strain, (2) supplemented with the Cbh1N209D, (3) or with the mutant N209E. All the measurements were analysed in duplicate and the error bars correspond to the standard deviation.

The results obtained are shown in FIG. 17, where it can be observed that the addition of the Cbh1N209D protein releases approximately 4% more glucose than the parental protein. The addition of a protein with the exchange of amino acid N209 for another amino acid (N209E) gave rise to an increase in the release of glucose of 7% with respect to the parental protein.

The invention claimed is:

1. A cellobiohydrolase 1 variant comprising the amino acid sequence set forth in SEQ ID NO: 6 or SEQ ID NO: 9, wherein the cellobiohydrolase 1 variant has greater cellobiohydrolase activity compared to the cellobiohydrolase 1 consisting of SEQ ID NO: 3.

2. The cellobiohydrolase 1 variant according to claim 1, which consists of the amino acid sequence SEQ ID NO: 6 or SEQ ID NO: 9.

3. The cellobiohydrolase 1 variant according to claim 1, which consists of the amino acid sequence SEQ ID NO: 5 or SEQ ID NO: 8.

4. A genetic construct comprising an isolated nucleic acid sequence that encodes the cellobiohydrolase 1 variant according to claim 1.

5. A host cell comprising the genetic construct according to claim 4.

6. The host cell according to claim 5, wherein said cell is *Myceliophthora thermophila* C1.

7. An enzyme composition comprising the cellobiohydrolase 1 variant according to claim 1.

8. The enzyme composition according to claim 7, which also comprises other cellulolytic enzymes.

9. The enzyme composition according to claim 8, wherein the other cellulolytic enzymes are selected from the list consisting of: endoglucanases, beta-glucosidases, cellobiohydrolases, beta-xylosidases, xyloglucanases, polysaccharide monooxygenases, xylanases, arabinofuranosidases and any combination thereof.

10. A procedure for producing fermentable sugars from cellulosic biomass comprising:
  a. Incubating the cellulosic biomass with the cellobiohydrolase 1 variant according to claim 1, and
  b. Recovering the fermentable sugars obtained after incubating in stage (a).

11. A procedure for producing fermentable sugars from cellulosic biomass comprising:

a. Incubating the cellulosic biomass with the host cell according to claim 5, and
b. Recovering the fermentable sugars obtained after incubating in stage (a).

12. A procedure for producing fermentable sugars from cellulosic biomass comprising:
  a. Incubating the cellulosic biomass with the enzyme composition according to claim 7, and
  b. Recovering the fermentable sugars obtained after incubating in stage (a).

13. A procedure for producing a bioproduct from cellulosic biomass comprising:
  a. Incubating the cellulosic biomass with the cellobiohydrolase 1 variant according to claim 1,
  b. Fermenting the fermentable sugars obtained after incubating in stage (a) with at least one fermenter microorganism, and
  c. Recovering the bioproduct obtained after fermenting in stage (b).

14. A procedure for producing a bioproduct from cellulosic biomass comprising:
  a. Incubating the cellulosic biomass with the host cell according to claim 5,
  b. Fermenting the fermentable sugars obtained after incubating in stage (a) with at least one fermenter microorganism, and
  c. Recovering the bioproduct obtained after fermenting in stage (b).

15. A procedure for producing a bioproduct from cellulosic biomass comprising:
  a. Incubating the cellulosic biomass with the enzyme composition according to claim 7,
  b. Fermenting the fermentable sugars obtained after incubating in stage (a) with at least one fermenter microorganism, and
  c. Recovering the bioproduct obtained after fermenting in stage (b).

16. The procedure according to claim 13, wherein the bioproduct is ethanol.

17. The procedure according to claim 14, wherein the bioproduct is ethanol.

18. The procedure according to claim 15, wherein the bioproduct is ethanol.

* * * * *